(12) United States Patent
Fukai et al.

(10) Patent No.: US 11,717,473 B2
(45) Date of Patent: Aug. 8, 2023

(54) SKIN CLEANSING AGENT CONTAINING A PARTICLE COMPRISED OF AN ESTER, MOISTURIZING AGENT, AND POLYMER

(71) Applicant: KAO CORPORATION, Tokyo (JP)

(72) Inventors: Shiho Fukai, Sumida-ku (JP); Kaori Umehara, Sumida-ku (JP); Toshiaki Ozawa, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 17/779,371

(22) PCT Filed: Nov. 24, 2020

(86) PCT No.: PCT/JP2020/043673
§ 371 (c)(1),
(2) Date: May 24, 2022

(87) PCT Pub. No.: WO2021/106874
PCT Pub. Date: Jun. 3, 2021

(65) Prior Publication Data
US 2022/0409504 A1    Dec. 29, 2022

(30) Foreign Application Priority Data

Nov. 25, 2019   (JP) .................................. 2019-212680

(51) Int. Cl.
| | | |
|---|---|---|
| *C11D 17/06* | (2006.01) | |
| *A61K 8/37* | (2006.01) | |
| *A61K 8/34* | (2006.01) | |
| *A61K 8/44* | (2006.01) | |
| *A61K 8/81* | (2006.01) | |
| *A61K 8/92* | (2006.01) | |
| *A61Q 19/10* | (2006.01) | |

(52) U.S. Cl.
CPC ................. *A61K 8/37* (2013.01); *A61K 8/34* (2013.01); *A61K 8/44* (2013.01); *A61K 8/81* (2013.01); *A61K 8/92* (2013.01); *A61Q 19/10* (2013.01)

(58) Field of Classification Search
CPC ..... C11D 17/06; C11D 3/2065; C11D 3/2093; C11D 3/37; C11D 3/43; C11D 7/266; C11D 7/5027; C11D 7/509; C11D 9/24
See application file for complete search history.

(56) References Cited

U.S. PATENT DOCUMENTS

| | | | | |
|---|---|---|---|---|
| 2003/0162838 A1* | 8/2003 | Yumioka | ................ | A01N 47/44 |
| | | | | 514/625 |
| 2004/0022818 A1* | 2/2004 | Cho | ..................... | A61K 8/9794 |
| | | | | 424/769 |
| 2004/0136942 A1 | 7/2004 | Yamazaki | | |
| 2010/0035831 A1* | 2/2010 | Matsunaga | ............ | A61K 8/604 |
| | | | | 514/25 |
| 2011/0004019 A1* | 1/2011 | Iida | ....................... | A61K 31/198 |
| | | | | 564/155 |
| 2012/0071568 A1* | 3/2012 | Sugiyama | .............. | A61K 8/891 |
| | | | | 510/159 |
| 2015/0366784 A1* | 12/2015 | Ramirez | ............... | A61K 8/9789 |
| | | | | 424/59 |
| 2016/0120768 A1* | 5/2016 | Morioka | .................. | A61Q 5/02 |
| | | | | 510/130 |
| 2016/0213594 A1* | 7/2016 | Katsuta | ................ | C11D 3/3719 |
| 2018/0042833 A1 | 2/2018 | Yan et al. | | |
| 2022/0023188 A1 | 1/2022 | Nonaka et al. | | |

FOREIGN PATENT DOCUMENTS

| | | |
|---|---|---|
| CN | 1976673 A | 6/2007 |
| JP | 5-229916 A | 9/1993 |
| JP | 10-513189 A | 12/1998 |
| JP | 2000-119171 A | 4/2000 |
| JP | 2004-262838 A | 9/2004 |
| JP | 2013-139402 A | 7/2013 |
| JP | 2014-76966 A | 5/2014 |
| JP | 2018-30836 A | 3/2018 |
| JP | 2020-94032 A | 6/2020 |
| WO | WO 96/24328 A1 | 8/1996 |
| WO | WO 2020/121958 A1 | 6/2020 |

OTHER PUBLICATIONS

International Search Report dated Feb. 2, 2021 in PCT/JP2020/043673 filed on Nov. 24, 2020, 2 pages.

* cited by examiner

Primary Examiner — Charles I Boyer
(74) Attorney, Agent, or Firm — Oblon, McClelland, Maier & Neustadt, L.L.P.

(57) ABSTRACT

A skin cleansing agent containing the following components (A), (B), and (C): a particle (A) including (A1), (A2), and (A3), (A1) a water-holding oil agent in an amount of from 0.0001 to 13 mass % in the skin cleansing agent, (A2) a moisturizing agent in an amount of from 0.001 to 25 mass % in the skin cleansing agent, and (A3) a polymer; a surfactant (B); and water (C).

12 Claims, No Drawings

SKIN CLEANSING AGENT CONTAINING A PARTICLE COMPRISED OF AN ESTER, MOISTURIZING AGENT, AND POLYMER

CROSS-REFERENCE TO RELATED APPLICATIONS

The present application is a 35 U.S.C. § 371 national stage application of International patent application PCT/JP2020/043673, filed Nov. 24, 2020, which is based on and claims the benefit of priority to Japanese Application No. 2019-212680, filed Nov. 25, 2019. The entire contents of these applications are incorporated herein by reference.

FIELD OF THE INVENTION

The present invention relates to a skin cleansing agent.

BACKGROUND OF THE INVENTION

Although skin cleansing agents are for cleaning the skin, many consumers are worried that their skin will dry out by using cleansing agents especially when washing the face. Consequently, skin cleansing agents for maintaining the moisturizing effect even after cleansing are being investigated.

For example, Patent Literature 1 discloses that a cosmetic cleansing composition containing a fatty acid ester of alkyl glycoside, an alkyl metal salt of alkyl sulfate, a fatty acid ester of alkoxylated sorbitan, and fatty acid dialkylolamide and being encapsulated in water-soluble capsules plentifully foams and is gentle to the skin.

Patent Literature 2 discloses that a gel cleansing agent composition containing a sucrose fatty acid ester, a polyhydric alcohol including three or more hydroxy groups in the molecule, and an oil has excellent stability over time, is easy to be rinsed out, and gives fresh feeling of use.

Patent Literature 3 discloses that a skin cleansing agent composition containing an anionic surfactant, a cationic polymer, and an oil agent having a specific viscosity has skin cleansing ability, leaves the oil agent on the skin after cleansing, and provides a moisturizing effect and a good feeling.

[Patent Literature 1]
JP-A-10-513189
[Patent Literature 2]
JP-A-5-229916
[Patent Literature 3]
JP-A-2004-262838

SUMMARY OF THE INVENTION

The present invention relates to a skin cleansing agent containing the following components (A), (B), and (C):
a particle (A) including (A1), (A2), and (A3):
  a water-holding oil agent (A1) in an amount of from 0.0001 to 13 mass % in the skin cleansing agent;
  a moisturizing agent (A2) in an amount of from 0.001 to 25 mass % in the skin cleansing agent; and
  a polymer (A3);
a surfactant (B); and
water (C).

In addition, the present invention relates to a method for cleansing a skin, including applying the skin cleansing agent to the skin, and then rinsing with water.

DETAILED DESCRIPTION OF THE INVENTION

Since skin cleansing agents are mainly purposed to remove dirt, such as sebum, sweat, and dust, on the skin, the compositions thereof are designed with emphasis on not leaving dirt on the skin, and the agents are used by washing out after application. Accordingly, even if a skin cleansing agent contains a large amount of a moisturizing component, it is difficult to sufficiently leave the moisturizing component on the skin to obtain a good feeling. In addition, a composition of which the main solvent is water has difficulty in safely incorporating an oily moisturizing component.

The present invention relates to a skin cleansing agent having excellent cleansing ability and rinsability, not giving a friction feeling or a stretched feeling after cleansing, giving a moist and soft skin feeling, and also having high storage stability.

The present inventors conceived an idea of obtaining a high moisture retaining property by leaving a water-holding oil agent and a moisturizing agent on the skin and repeated studies to achieve both this moisture retaining property and the cleansing property required by the skin cleansing agent. As a result, it was found that a skin cleansing agent having excellent cleansing ability and rinsability, not giving a friction feeling and a stretched feeling after cleansing, giving a moist and soft skin feeling, and also having good storage stability can be obtained when a water-holding oil agent and a moisturizing agent are contained in particle forms, and the present invention was accomplished.

The skin cleansing agent of the present invention has excellent cleansing ability and rinsability, not giving a friction feeling and a stretched feeling after cleansing, giving a moist and soft skin feeling which is also maintained for a long time. In addition, even in a water-based prescription, the oily component is stably contained without being separated, and the storage stability is also good.

The particle of the component (A) used in the present invention includes a water-holding oil agent (A1), a moisturizing agent (A2), and a polymer (A3).

The water-holding oil agent (A1) is an oil agent which has a water-holding capacity equal to or more than its own weight (100% or more) and is an oil agent which can hold water equal to or more than its own weight at 50° C. In the present invention, the water-holding capacity is an indicator showing how much water the oil agent at 50° C. can hold and is evaluated as follows. That is, 10 g of a sample (oily component) heated to 50° C. is weighed in a 200-mL beaker. Water at 50° C. is gradually added thereto while being stirred with a disper mixer at 3 000 r/min until water is drained from the sample. The amount (mass) of the water added to the sample before the start of draining water from the sample is measured. The added amount is divided by the mass of the sample of 10 g to obtain a quotient. The value obtained by multiplying the quotient by 100 is the water-holding capacity (%).

Examples of the water-holding oil agent include dimer acid esters, glycerol fatty acid esters, pentaerythritol fatty acid esters, fatty acid cholesterol esters having from 16 to 22 carbon atoms, phytosterol esters having from 16 to 22 carbon atoms, and N-acyl amino acid esters.

Examples of the dimer acid ester include esters of dimer acids and alcohols. An ester of dimer dilinoleic acid is preferable, and an ester of dimer dilinoleic acid and dimer diol is more preferable. The ester moiety of dimer acid or dimer dilinoleic acid preferably includes one or more moieties selected from the group consisting of behenyl, isostearyl, stearyl, cetyl, and phytosteryl and more preferably includes one or more moieties selected from the group consisting of behenyl, isostearyl, stearyl, cetyl, and phytosteryl. Further specifically, for example, bis(behenyl/isostearyl/phytosteryl) dimer dilinoleyl dimer dilinoleate, bis(phytosteryl/isostearyl/cetyl/stearyl/behenyl) dimer dilinoleyl dimer dilinoleate, phytosteryl/isostearyl/cetyl/stearyl/behenyl dimer dilinoleate, di(isostearyl/phytosteryl) dimer dilinoleate, and dimer dilinoleyl diisostearate are mentioned, and phytosteryl/isostearyl/cetyl/stearyl/behenyl dimer dilinoleate and di(isostearyl/phytosteryl) dimer dilinoleate are preferably mentioned.

Examples of the glycerol fatty acid ester include glyceryl diisostearate, diglyceryl triisostearate, and tetraglyceryl pentastearate.

Examples of the pentaerythritol fatty acid ester include pentaerythrityl tetra(behenate/benzoate/ethylhexanoate), pentaerythrityl tetra(ethylhexanoate/benzoate), dipentaerythrityl tripolyhydroxystearate, dipentaerythrityl hexa (hydroxystearate/stearate/rosinate), dipentaerythrityl hydroxystearate/isostearate, dipentaerythrityl hexahydroxystearate, pentaerythrityl tetraethylhexanoate, pentaerythrityl tetraisostearate, dipentaerythritol 12-hydroxystearate/stearate/rosinate, and dipentaerythritol 12-hydroxystearate/isostearate.

Examples of the fatty acid cholesterol ester having from 16 to 22 carbon atoms include a palmitic acid cholesterol ester, cholesteryl hydroxystearate, a stearic acid cholesterol ester, a behenic acid cholesterol ester, an isostearic acid cholesterol ester, an oleic acid cholesterol ester, a palmitooleic acid cholesterol ester, a behenic acid cholesterol ester, a linoleic acid cholesterol ester, and a linolenic acid cholesterol ester. The fatty acid used may be a mixed fatty acid and may be, for example, a sunflower seed oil fatty acid cholesterol ester or a macadamia nut oil fatty acid cholesterol ester.

Examples of the phytosterol ester having from 16 to 22 carbon atoms include a palmitic acid phytosterol ester, a stearic acid phytosterol ester, a behenic acid phytosterol ester, an isostearic acid phytosterol ester, an oleic acid phytosterol ester, a palmitooleic acid phytosterol ester, a behenic acid phytosterol ester, a linoleic acid phytosterol ester, and a linolenic acid phytosterol ester. The fatty acid may be a mixed fatty acid and may be, for example, a sunflower seed oil fatty acid phytosterol ester or a macadamia nut oil fatty acid phytosterol ester.

The number of carbon atoms of the acyl group in the N-acyl amino acid ester is preferably from 10 to 30 and more preferably from 12 to 18. The acyl group may be saturated or unsaturated. The acyl group may be derived from a mixed fatty acid, and examples thereof include a cocoyl fatty acid ester, a palm oil fatty acid ester, a palm kernel oil fatty acid ester, a sunflower seed oil fatty acid ester, and a macadamia nut oil fatty acid ester.

The N-acyl amino acid ester is preferably an alkyl ester of N-acylamino acid. The number of carbon atoms of the alkyl group constituting the alkyl ester is preferably from 1 to 30 and more preferably from 12 to 18. The alkyl group may be branched or linear or may have a cyclic structure. Examples of such N-acyl amino acid esters include di(cholesteryl/behenyl/octyldodecyl) N-lauroyl-L-glutamate, di(phytosteryl/behenyl/octyldodecyl) N-lauroyl-L-glutamate, and phytosteryl/decyltetradecyl N-myristoyl-N-methylalanine.

As the component (A1), a pentaerythritol fatty acid ester and a fatty acid cholesterol ester are more preferable, a pentaerythritol fatty acid ester is further more preferable, and dipentaerythrityl tripolyhydroxystearate is even more preferable, from the viewpoint of maintaining the moist feeling and the non-stretched feeling after cleaning and maintaining the softness of the skin after cleansing due to a high water-holding property, miscibility with the moisturizing agent, and its high tendency to remain on the skin also after rinsing with water.

As the component (A1), water-holding oil agents can be used alone or in combination of two or more thereof, and the content thereof in the skin cleansing agent is, from the viewpoint of persistence of the moisture retaining ability after cleansing, 0.0001 mass % or more, preferably 0.001 mass % or more, more preferably 0.01 mass % or more, and further more preferably 0.03 mass % or more and is, from the viewpoint of improving the rinsability, suppressing the stickiness during and after cleansing, and improving the storage stability of the cleansing agent, 13 mass % or less, preferably 10 mass % or less, more preferably 5 mass % or less, further more preferably 2 mass % or less, and even more preferably 1 mass % or less. The content of the water-holding oil agent (A1) in the skin cleansing agent is from 0.0001 to 13 mass %, preferably from 0.0001 to 10 mass %, more preferably from 0.001 to 5 mass %, further more preferably from 0.01 to 2 mass %, and even more preferably from 0.03 to 1 mass %.

The moisturizing agent (A2) is that used in general cosmetics and may be either oily or water-soluble.

Examples of the oily moisturizing agent include oil agents which are liquid or solid at 25° C.

The oil agent is not limited as long as it is one which is used in general skin cosmetics, and examples thereof include linear or branched hydrocarbon oils, such as squalene, squalane, liquid paraffin, liquid isoparaffin, heavy liquid isoparaffin, an α-olefin oligomer, cycloparaffin, polybutene, petrolatum, paraffin wax, microcrystalline wax, polyethylene wax, and cerecin; ester oils, such as isononyl isononanoate, isodecyl isononanoate, isotridecyl isononanoate, tricyclodecanemethyl isononanoate, ethyl isostearate, isobutyl isostearate, isopropyl isostearate, 2-hexyldecyl isostearate, isostearyl isostearate, di(2-ethylhexyl) succinate, bis-ethoxydiglycol succinate, hexyl laurate, propanediol di(caprylate/caprate), neopentyl glycol diisononanoate, neopentyl glycol dicaprate, glyceryl diisostearate, polyglyceryl diisostearate, propanediol diisostearate, trimethylolpropane triisostearate, glyceryl triisostearate, diglyceryl triisostearate, diglyceryl tetraisostearate, diisostearyl malate, octyldodecyl malate, a glycerol fatty acid ester, jojoba oil, di(phytosteryl/octyldodecyl) lauroyl glutamate, octyldodecyl myristate, isopropyl myristate, 2-ethylhexyl palmitate, isopropyl palmitate, cetyl 2-ethylhexanoate, trimethylolpropane tri(2-ethylhexanoate), glyceryl tri(2-ethylhexanoate), octyldodecyl myristate, 2-hexyldecyl myristate, 2-hexyldecyl 2-ethylhexanoate, neopentyl glycol di(2-ethylhexanoate), 2-ethylhexyl hydroxystearate, glyceryl tri(capryl/caprate), glyceryl trioctanoate, and neopentyl glycol dioctanoate; and higher alcohols, such as lauryl alcohol, oleyl alcohol, isostearyl alcohol, behenyl alcohol, and octyl dodecanol.

Among these agents, from the viewpoint of further enhancing the skin softening effect after cleansing and also the high moisture confining property and the moist feeling and the non-stretched feeling after cleansing and maintaining the softness of the skin, a hydrocarbon oil is preferable, and squalane and petrolatum are more preferable.

Examples of the water-soluble moisturizing agent include polyhydric alcohols.

Examples of the polyhydric alcohol include divalent alcohols, such as ethylene glycol, diethylene glycol, hexylene glycol, polyethylene glycol having an average molecular weight of 10 000 or less, propylene glycol, 1,3-propanediol, dipropylene glycol, polypropylene glycol, isoprene glycol, and 1,3-butylene glycol; tri- or higher valent alcohols, such as glycerol, diglycerol, triglycerol, tetraglycerol, hexaglycerol, decaglycerol, and trimethylpropanol; and sugars or sugar alcohols, such as erythritol, pentaerythritol, dipentaerythritol, glucose, mannose, galactose, sucrose, fructose, maltose, maltitol, xylitol, inositol, sorbitan, and sorbitol.

Among these agents, from the viewpoint of improving the moist feeling after cleansing, glycerol is preferable.

As the component (A2), from the viewpoint of further improving the moisture retaining property after cleansing and further increasing the persistence of the moist feeling after cleansing, it is preferable to include an oily moisturizing agent and more preferable to include a hydrocarbon oil, preferably one or more selected from the group consisting of squalane and petrolatum, and it is more preferable to use a combination of squalane and petrolatum.

As the component (A2), moisturizing agents can be used alone or in combination of two or more thereof, and the content thereof in the skin cleansing agent is, from the viewpoint of persistence of the moisture retaining ability after cleansing, 0.001 mass % or more, preferably 0.01 mass % or more, more preferably 0.02 mass % or more, and further more preferably 0.05 mass % or more and is, from the viewpoint of improving the rinsability, suppressing the stickiness during and after cleansing, and improving the storage stability of the cleansing agent, 25 mass % or less, preferably 20 mass % or less, more preferably 10 mass % or less, further more preferably 5 mass % or less, and even more preferably 2 mass % or less. The content of the moisturizing agent (A2) in the skin cleansing agent is from 0.001 to 25 mass %, preferably from 0.001 to 20 mass, more preferably from 0.01 to 10 mass %, further more preferably from 0.02 to 5 mass %, and even more preferably from 0.05 to 2 mass %.

In the component (A), a mass ratio of the (A1) to the (A2), (A1)/(A2), is, from the viewpoint of reducing the friction feeling after cleansing and satisfying the moist feeling, non-stretched feeling, and softness simultaneously as the skin feeling that is maintained after cleansing, preferably 0.004 or more, more preferably 0.005 or more, further more preferably 0.01 or more, even more preferably 0.05 or more, and even more preferably 0.15 or more and is preferably 60 or less, more preferably 50 or less, further more preferably 30 or less, even more preferably 20 or less, and even more preferably 1 or less. In addition, the mass ratio of the (A1) to the (A2), (A1)/(A2), is preferably from 0.004 to 60, more preferably from 0.005 to 50, further more preferably from 0.01 to 30, even more preferably from 0.05 to 20, and even more preferably from 0.15 to 1.

The particle of the component (A) further includes a polymer (A3).

In the component (A), the (A1) and the (A2) may be encapsulated in the polymer particle as the (A3) and/or may be dotted on the surface of the (A3) or may be dispersed in the particle.

From the viewpoint of suppressing aggregation between particles and improving the storage stability of the cleansing agent, the (A1) and the (A2) are preferably disposed inside the particle, for example, preferably encapsulated or dispersed in the particle. The phrase "the (A1) and the (A2) are disposed inside the particle" encompasses not only a state in which the (A1) and the (A2) are completely absent on the particle surface but also a state in which the (A1) and the (A2) are mostly disposed inside the particle and partly adhere to the particle surface.

It is inferred that when the cleansing agent contains a particle constituted of these components (A1), (A2), and (A3), in spite of using one cleansing agent, the components (A1) and (A2) are adsorbed to the skin after cleansing dirt, such as sebum, on the skin surface to increase the moisture retaining property and realize the persistence of the moist feeling and the softness of the skin.

The polymer (A3) is, from the viewpoint of removing dirt, such as sebum, and giving a moist feeling after washing, preferably a polymer whose particles disintegrate or dissolve during application of the skin cleansing agent to the skin or during rinsing. For example, a hydrophilic polymer is preferable. Furthermore, the hydrophilic polymer is preferably a polymer of which the solubility changes depending on the concentration of water-soluble salts (hereinafter, referred to as salt-sensitive polymer).

Here, the term "salt-sensitive polymer" refers to a polymer of which a sheet of 2 cm×2 cm is completely dissolved in water having a salt concentration of 1% when visually verified after stirring at 25° C. for 5 minutes but is not dissolved in water having a salt concentration of 10% when visually verified after the same test is performed.

When a salt-sensitive polymer is included as the (A3), the particle of the component (A) becomes a particle (hereinafter, referred to as salt-sensitive particle) of which the solubility is improved by a decrease in the concentration of the water-soluble salts (e.g., sodium chloride) in the composition containing the particle. When a skin cleansing agent contains this salt-sensitive particle, since the concentration of water-soluble salts in the skin cleansing agent is high, the particle does not disintegrate, and the components (A1) and (A2) are stably present in the particle. However, when the concentration of the water-soluble salts in the skin cleansing agent is decreased in the process of applying the skin cleansing agent to the skin and in the process of rinsing, the solubility in water is improved, the particle disintegrates, and the components (A1) and (A2) are released. Then, the components (A1) and (A2) included in the salt-sensitive particle are likely to remain on the skin after the dirt on the skin has been removed. Accordingly, it is inferred that when a salt-sensitive polymer is included in the (A3), a more preferable result is obtained.

That is, in the skin cleansing agent of the present invention, when a salt-sensitive particle in which a water-holding oil agent as the component (A1) and a moisturizing agent as the component (A2) are dispersed is used, the skin cleansing agent is diluted when the cleansing agent is applied to the skin to decrease the salt concentration, which reduces the particle strength, and also physical force is applied by the fingers etc., resulting in easy disintegration of the particle and easy release of the components (A1) and (A2) in the particle. Furthermore, the cleansing agent is further diluted during rinsing to further decrease the salt concentration, which makes the particle further easily disintegrate and the components (A1) and (A2) in the particle easily released. Accordingly, the water-holding oil agent (A1) and the moisturizing agent (A2) are likely to remain on the skin after the dirt, such as sebum, has been removed, the feeling of the moisturizing effect can be further improved.

When a water-holding oil agent and a moisturizing agent are dispersed in a salt-sensitive particle, in comparison with the same amount, it is inferred that a particle containing the water-holding oil agent and the moisturizing agent more finely dispersed therein is likely to uniformly adhere to the skin to improve the feeling of the effect. Since the water-holding oil agent and the moisturizing agent are contained in the salt-sensitive particle, a skin cleansing agent containing the particle can prevent these components from separating and also has excellent storage stability.

Thus, when the component (A) is a salt-sensitive particle, as the polymer, an acid-modified polyvinyl alcohol is preferably used. The acid-modified polyvinyl alcohol is a polyvinyl alcohol including an acid group, such as a sulfonic acid group, a sulfuric acid group, a carboxylic acid group, a phosphic acid group, and a phosphonic acid group, and is, from the viewpoint of the storage stability in the skin cleansing agent and the disintegration due to a decrease in the concentration of water-soluble salts during cleansing (during cleansing and during rinsing), more preferably an acid-modified polyvinyl alcohol having introduced therein one or more selected from the group consisting of a sulfuric acid group and a carboxylic acid group and further more preferably an acid-modified polyvinyl alcohol having introduced therein a carboxylic acid group (hereinafter, also referred to as "carboxylic acid-modified polyvinyl alcohol").

Examples of the carboxylic acid-modified polyvinyl alcohol include (1) one obtained by graft polymerization or block polymerization of a polyvinyl alcohol and an unsaturated monomer including a carboxy group, (2) one obtained by copolymerizing a vinyl ester compound and an unsaturated monomer including at least one selected from the group consisting of a carboxy group (carboxylic acid group) and a carboxylic acid ester group and then performing saponification, (3) one obtained by polymerizing a vinyl ester compound using a chain transfer agent including a carboxy group and then performing saponification, and (4) one obtained by reacting a carboxylating agent with a polyvinyl alcohol.

Examples of the unsaturated monomer including a carboxy group used in the above methods (1) and (2) and the unsaturated monomer including a carboxylic acid ester group used in the above method (2) include ethylene unsaturated dicarboxylic acids, such as maleic acid, fumaric acid, and itaconic acid; ethylene unsaturated dicarboxylic acid monoesters, such as a maleic acid monoalkyl ester, a fumaric acid monoalkyl ester, and an itaconic acid monoalkyl ester; ethylene unsaturated dicarboxylic acid diesters, such as a maleic acid dialkyl ester, a fumaric acid dialkyl ester, and an itaconic acid dialkyl ester; ethylene unsaturated carboxylic anhydrides, such as maleic anhydride and itaconic anhydride; unsaturated monocarboxylic acids, such as (meth) acrylic acid; and unsaturated monocarboxylic acid esters, such as a (meth)acrylic acid alkyl ester. As the unsaturated monomer including at least one selected from the group consisting of a carboxy group and a carboxylic acid ester group, a salt of any of the above-mentioned compounds may be used.

Among these compounds, from the viewpoint of reactivity, ethylene unsaturated carboxylic acid monoester is preferable, ethylene unsaturated dicarboxylic acid monoester is more preferable, a maleic acid monoalkyl ester and an itaconic acid monoalkyl ester are further more preferable, and a maleic acid monoalkyl ester is even more preferable.

These compounds may be used alone or in combination of two or more thereof.

Examples of the vinyl ester compound used in the above methods (2) and (3) include vinyl acetate, vinyl formate, vinyl propionate, vinyl versatate, and vinyl pivalate. Among these compounds, vinyl acetate is preferable from the viewpoint of the reactivity during synthesis and the ease of acquisition.

These compounds may be used alone or in combination of two or more thereof.

Examples of the carboxylating agent used in the above method (4) include carboxylic anhydrides, such as succinic anhydride, maleic anhydride, acetic anhydride, trimellitic anhydride, phthalic anhydride, pyromellitic anhydride, glutaric anhydride, hydrogenated phthalic anhydride, and naphthalene dicarboxylic anhydride.

These agents may be used alone or in combination of two or more thereof.

The acid modification rate (the rate of a monomer including an acid group) in the acid-modified polyvinyl alcohol is, from the viewpoint of improving the releasability of the components (A1) and (A2) due to a decrease in the concentration of the water-soluble salts, preferably 0.1 mol % or more, more preferably 0.5 mol % or more, and further more preferably 1 mol % or more and is, from the viewpoint of the storage stability of the component (A) in the skin cleansing agent, preferably 10 mol % or less, more preferably 5 mol % or less, and further more preferably 3 mol % or less. Accordingly, the acid modification rate in the acid-modified polyvinyl alcohol is, from the viewpoint of improving the releasability of the components (A1) and (A2) due to a decrease in the concentration of the water-soluble salts and from the viewpoint of the storage stability of the component (A) in the skin cleansing agent, preferably 0.1 mol % or more and 10 mol % or less, more preferably 0.5 mol % or more and 5 mol % or less, and further more preferably 1 mol % or more and 3 mol % or less.

The acid modification rate in the acid-modified polyvinyl alcohol can be determined by analyzing the acid-modified polyvinyl alcohol before saponification using 1H-NMR (solvent: $CDCl_3$).

The degree of saponification of the acid-modified polyvinyl alcohol is, from the viewpoint of the storage stability of the component (A) in the skin cleansing agent, preferably 70 mol % or more, more preferably 80 mol % or more, and further more preferably 90 mol % or more and is, from the viewpoint of improving the releasability of the components (A1) and (A2) due to a decrease in the concentration of the water-soluble salts, preferably 99.9 mol % or less, more preferably 99.5 mol % or less, and further more preferably 99 mol % or less. Accordingly, from the viewpoint of improving the releasability of the components (A1) and (A2) due to a decrease in the concentration of the water-soluble salts and from the viewpoint of the storage stability of the component (A) in the skin cleansing agent, the degree of saponification of the acid-modified polyvinyl alcohol is preferably 70 mol % or more and 99.9 mol % or less, more preferably 80 mol % or more and 99.5 mol % or less, and further more preferably 90 mol % or more and 99 mol % or less.

The degree of saponification of the acid-modified polyvinyl alcohol is measured in accordance with JIS K6726: 1994.

The degree of polymerization of the acid-modified polyvinyl alcohol is, from the viewpoint of the storage (granules) stability of the component (A) in the skin cleansing agent, preferably 100 or more, more preferably 500 or more, and further more preferably 1,000 or more and is, from the viewpoint of improving the releasability of the components (A1) and (A2) due to a decrease in the concentration of the water-soluble salts, preferably 200,000 or less, more preferably 10,000 or less, and further more preferably 4,000 or less. Accordingly, from the viewpoint of improving the releasability of the components (A1) and (A2) due to a decrease in the concentration of the water-soluble salts and from the viewpoint of the storage stability of the component (A) in the skin cleansing agent, the degree of polymerization of the acid-modified polyvinyl alcohol is preferably 100 or more and 200,000 or less, more preferably 500 or more and 10,000 or less, and further more preferably 1,000 or more and 4,000 or less.

The degree of polymerization of the acid-modified polyvinyl alcohol can be calculated from the relative viscosity of fully saponified polyvinyl alcohol aqueous solution and water (see JIS K6726: 1994).

The molecular weight of the acid-modified polyvinyl alcohol is, from the viewpoint of the storage stability of the component (A) in the skin cleansing agent, preferably 5 000 or more, more preferably 10 000 or more, further more preferably 30 000 or more, and even more preferably 50 000 or more and is, from the viewpoint of the releasability of the components (A1) and (A2) due to a decrease in the concentration of the water-soluble salts, preferably 1 000 000 or less, more preferably 500,000 or less, and further more preferably 200 000 or less. Accordingly, from the viewpoint of improving the releasability of the components (A1) and (A2) due to a decrease in the concentration of the water-soluble salts and the viewpoint of the storage stability of the salt-sensitive particle in the skin cleansing agent, the molecular weight of the acid-modified polyvinyl alcohol is preferably 5 000 or more and 1 000 000 or less, more preferably 10 000 or more and 500 000 or less, further more preferably 30 000 or more and 200 000 or less, and even more preferably 50 000 or more and 200 000 or less.

The molecular weight of the acid-modified polyvinyl alcohol can be determined by calculation from the degree of polymerization.

Specifically, examples of the acid-modified polyvinyl alcohol include KL-118, KL-318, KL-506, KM-118, and KM-618 manufactured by Kuraray Co., Ltd.; GOHSENX CKS50, GOHSENX T-330H, GOHSENX T-330, and GOHSENX T-350 manufactured by Mitsubishi Chemical Corporation; and AP-17, AT-17, and AF-17 manufactured by Japan Vam & Poval Co., Ltd.

The particle of the component (A) can further contain, for example, a water-insoluble particle, a surfactant, a colorant (such as a dye and a pigment), a preservative, a fragrance, a thickener, a cooling sensation agent, an astringent agent, a bactericide, a UV absorber, a whitening agent, and an anti-inflammatory agent.

The content of the acid-modified polyvinyl alcohol in the component (A) is, from the viewpoint of showing the effect of salt sensitivity, preferably 1 mass % or more, more preferably 5 mass % or more, further more preferably 10 mass % or more, even more preferably 20 mass % or more, and further more preferably 40 mass % or more and is, from the viewpoint of containing other components, such as the components (A1) and (A2), preferably 99 mass % or less, more preferably 95 mass % or less, further more preferably 90 mass % or less, even more preferably 85 mass % or less, and further more preferably 80 mass % or less.

The content of the acid-modified polyvinyl alcohol in the component (A) is, from the viewpoint mentioned above, preferably 1 mass % or more and 99 mass % or less, more preferably 5 mass % or more and 95 mass % or less, further more preferably 10 mass % or more and 90 mass % or less, even more preferably 20 mass % or more and 85 mass % or less, and further more preferably 40 mass % or more and 80 mass % or less.

The acid-modified polyvinyl alcohol forms a matrix of the component (A). That is, it is a polymer component corresponding to the sea part of a sea-island structure. As the polymer component of the component (A3), in addition to the acid-modified polyvinyl alcohol, another polymer and another additive may be contained. The content of the acid-modified polyvinyl alcohol in the component (A3) is, from the viewpoint of obtaining good salt sensitivity, preferably 50 mass % or more, more preferably 70 mass % or more, further more preferably 90 mass % or more, and even more preferably 95 mass % or more and may be 100 mass %.

The content of the components (A1) and (A2) in the component (A) is, from the viewpoint of showing the effect of the components (A1) and (A2), preferably 0.1 mass % or more, more preferably 0.5 mass % or more, further more preferably 1 mass % or more, even more preferably 5 mass % or more, and further more preferably 10 mass % or more and is, from the viewpoint of preventing the components (A1) and (A2) from leaking from the component (A), preferably 80 mass % or less, more preferably 70 mass % or less, further more preferably 60 mass % or less, even more preferably 50 mass % or less, and further more preferably 40 mass % or less.

The content of the components (A1) and (A2) in the component (A) is, from the viewpoint mentioned above, preferably from 0.1 to 80 mass %, more preferably from 0.5 to 70 mass %, further more preferably from 1 to 60 mass %, even more preferably from 5 to 50 mass %, and further more preferably from 10 to 40 mass %.

A mass ratio of the content of the acid-modified polyvinyl alcohol to the content of the components (A1) and (A2) in the component (A), (acid-modified polyvinyl alcohol/the components (A1) and (A2)), is, from the viewpoint of preventing the components (A1) and (A2) from leaking from the component (A), preferably 0.1 or more, more preferably 0.3 or more, further more preferably 0.5 or more, even more preferably 0.7 or more, and further more preferably 1 or more and is, from the viewpoint of efficiently containing the components (A1) and (A2), preferably 90 or less, more preferably 70 or less, further more preferably 50 or less, even more preferably 30 or less, and further more preferably 10 or less.

The component (A) can contain, in addition to the (A1) and the (A2), oily components, such as the above-mentioned fragrance, surfactant, and UV absorber (hereinafter, the (A1), the (A2), and other oily components are collectively referred to as an oil agent). A mass ratio of the acid-modified polyvinyl alcohol to the oil agent in the component (A) is, from the viewpoint mentioned above, preferably from 0.1 to 90, more preferably from 0.3 to 70, further more preferably from 0.5 to 50, even more preferably from 0.7 to 30, and further more preferably from 1 to 10.

An average particle diameter (dried product physical property) of the component (A) is, from the viewpoint of the feeling of use in the case where the skin cleansing agent contains it, preferably 1 500 μm or less, more preferably 1 000 μm or less, further more preferably 500 μm or less, even more preferably 200 μm or less, and further more preferably 100 μm or less and is, from the viewpoint of containing the components (A1) and (A2), preferably 1 μm or more, more preferably 5 μm or more, further more preferably 10 μm or more, even more preferably 20 μm or more, and further more preferably 30 μm or more.

The average particle diameter (dried product physical property) of the component (A) is, from the viewpoint mentioned above, preferably from 1 to 1 500 μm, more preferably from 5 to 1 000 μm, further more preferably from 10 to 500 μm, even more preferably from 20 to 200 μm, and further more preferably from 30 to 100 μm.

In the present invention, the average particle diameter of the component (A) is measured by using a laser diffraction/scattering particle size distribution analyzer LA-920 (manufactured by HORIBA, Ltd.), and the median diameter is defined as the average particle diameter.

The component (A) can be manufactured by, for example, removing water from an emulsified composition containing the components (A1) and (A2) and the component (A3).

The method for manufacturing the component (A) preferably includes the following step 1 and step 2 in this order:
Step 1: a step of preparing an emulsified composition containing the components (A1) and (A2) and the component (A3); and
Step 2: a step of removing water from the emulsified composition.

Step 1 preferably includes the following steps 1-1 to 1-3:
Step 1-1: a step of preparing an oil phase containing the components (A1) and (A2);
Step 1-2: a step of preparing an aqueous phase containing the component (A3); and
Step 1-3: a step of mixing the two liquids prepared in step 1-1 and step 1-2 to obtain an emulsified composition.

Step 1-1 is a step of preparing an oil phase containing the components (A1) and (A2).

In step 1-1, although an oil phase may be prepared by heating and melting the components (A1) and (A2) separately, a surfactant, an emulsion aid as needed, and other components, such as an oily component optionally contained in the component (A) are preferably added to and dissolved or dispersed in the components (A1) and (A2) to prepare an oil phase.

In step 1-2, the component (A3), water, and other components as needed are mixed and dissolved to prepare an aqueous phase.

In step 1-3, an emulsified composition is prepared by preferably mixing the oil phase and the aqueous phase prepared in advance with stirring.

The emulsion diameter is, from the viewpoint of increasing the survival rate of the components (A1) and (A2), the viewpoint of increasing the manufacturing yield, and the viewpoint of decreasing the average particle diameters of the components (A1) and (A2) in the resulting component (A) to show the effects of the components (A1) and (A2), preferably from 0.01 to 100 µm, more preferably from 0.05 to 50 µm, further more preferably from 0.1 to 30 µm, even more preferably from 0.1 to 10 µm, further more preferably from 0.1 to 5 µm, and even more preferably from 0.1 to 1 µm.

As the emulsifier, it is preferable to use a general stirrer such as a static emulsifier/disperser, a propeller blade, and a flat blade, a stirring emulsifier such as a homo mixer and a disper mixer, and a high pressure emulsifier such as homogenizer and a nanomizer.

In the emulsification, it is preferable to use a surfactant together with the oil phase containing the components (A1) and (A2), from the viewpoint of reducing the emulsion diameter to finely disperse the oil phase containing the components (A1) and (A2) in the component (A), and preferable examples of the surfactant include anionic surfactants and nonionic surfactants. The surfactant content with respect to 100 parts by mass of the oil phase containing the components (A1) and (A2) is, from the viewpoint of finely dispersing the oil phase component in the component (A), preferably 0.3 parts by mass or more, more preferably 1 part by mass or more, and further more preferably 3 parts by mass or more and preferably 50 parts by mass or less, more preferably 25 parts by mass or less, and further more preferably 15 parts by mass or less. The surfactant content in the component (A) with respect to 100 parts by mass of the oil phase containing the components (A1) and (A2) is, from the viewpoint mentioned above, preferably from 0.3 to 50 parts by mass, more preferably from 1 to 25 parts by mass, and further more preferably from 3 to 15 parts by mass.

When the component (A) contains a water-insoluble particle, after the preparation of an emulsified composition in step 1-3, the water-insoluble particle is preferably added to the emulsified composition.

Step 2 is a step of removing water from the emulsified composition prepared in step 1.

Examples of the method for removing water include spray drying, freeze drying, vacuum drying, belt drying, shelf drying, and drum drying. From the viewpoint of easily adjusting the particle shape and the storage stability of the oily component in the component (A), spray drying is preferable. When drying is performed by a method other than spray drying, as needed, pulverization is performed for obtaining a particle with a desired particle diameter.

Examples of the granulation method include rolling granulation, rolling fluidized granulation, fluidized bed granulation, and stirring rolling granulation.

When a water-insoluble particle is used, the particle can be added to the emulsified composition in step 1. Alternatively, a step 1' of mixing the emulsified composition obtained in step 1 and the water-insoluble particle and performing granulation can also be used.

When a granulated product is prepared in step 1', for example, freeze drying, vacuum drying, or shelf drying is preferably performed.

The particle of the component (A) may be used in a single kind or two or more kinds in combination, and the content in the skin cleansing agent is, from the viewpoint of the moisture retaining ability and the persistence thereof, preferably 0.001 mass % or more, more preferably 0.01 mass % or more, and further more preferably 0.1 mass % or more and is, from the viewpoint of being uniformly contained in the skin cleansing agent, preferably 50 mass % or less, more preferably 20 mass % or less, and further more preferably 10 mass % or less. In addition, the content of the component (A) in the skin cleansing agent is preferably from 0.001 to 50 mass %, more preferably from 0.01 to 20 mass %, and further more preferably from 0.1 to 10 mass %.

The surfactant as the component (B) may be any surfactant that is used in general cleansing agents, and examples thereof include an anionic surfactant, a cationic surfactant, a nonionic surfactant, and an amphoteric surfactant.

As the surfactant, one or more selected from the group consisting of anionic surfactants and nonionic surfactants are preferably contained from the viewpoint of cleansing property and the skin feeling during and after cleansing.

The anionic surfactant is preferably an anionic surfactant including a hydrocarbon group preferably having from 12 to 24 carbon atoms, more preferably 12 to 16 carbon atoms, and further more preferably 12 to 14 carbon atoms, and examples thereof include fatty acid salts having from 12 to 24 carbon atoms, such as sodium laurate, potassium laurate, and potassium palmitate; polyoxyethylene alkyl ether carboxylates, such as sodium polyoxyethylene tridecyl ether acetate; alkyl phosphates, such as potassium lauryl phosphate, sodium lauryl phosphate, arginine lauryl phosphate, potassium myristyl phosphate, sodium myristyl phosphate, arginine myristyl phosphate, potassium palmityl phosphate, sodium palmityl phosphate, and arginine palmityl phosphate; polyoxyethylene alkyl ether phosphates, such as sodium polyoxyethylene oleyl ether phosphate and sodium polyoxyethylene stearyl ether phosphate; alkylsulfuric acid ester salts, such as sodium lauryl sulfate and potassium lauryl sulfate; polyoxyethylene alkyl ether sulfuric acid ester salts, such as potassium polyoxyethylene lauryl sulfate, sodium polyoxyethylene lauryl sulfate, and polyoxyethylene lauryl sulfate triethanolamine; acylated amino acid salts, such as sodium lauroyl sarcosine, monosodium N-lauroyl glutamate, disodium N-stearoyl glutamate, monosodium N-myristoyl-L-glutamate, N-lauroyl glycine triethanolamine, N-coconut oil fatty acid acylglycine potassium salt, N-lauroyl-β-alanine triethanolamine, and N-stearoyl-β-alanine triethanolamine; fatty acid amide sulfonates, such as sodium N-myristoyl-N-methyltaurate and sodium N-stearoyl-N-methyltaurate; and sulfosuccinates, such as sodium di-2-ethylhexylsulfosuccinate.

Among these anionic surfactants, from the viewpoint of the cleansing property and gentleness to the skin, an acylated amino acid salt and a polyoxyethylene alkyl ether carboxylate are preferable.

Examples of the nonionic surfactant include sorbitan fatty acid esters, such as sorbitan monostearate; polyglycerol fatty acid esters, such as a glycerol fatty acid ester and polyglyceryl monoisostearate; polyoxyethylene fatty acid esters, such as a propylene glycol fatty acid ester and polyethylene glycol monolaurate; sucrose fatty acid esters; polyoxyethylene sorbitan fatty acid esters, such as polyoxyethylene sorbitan monostearate, polyoxyethylene sorbitan monostearate, and polyoxyethylene coconut oil fatty acid sorbitan; polyoxyethylene alkyl ethers; polyoxyethylene sorbitol fatty acid esters; polyoxyethylene glycerol fatty acid esters; polyoxyethylene propylene glycol fatty acid esters; polyoxyethylene castor oil; polyoxyethylene hydrogenated castor oil; polyoxyethylene hydrogenated castor oil fatty acid esters; alkyl polyglucosides; and polyoxyalkylene-modified silicone, such as a polyoxyethylene-methylpolysiloxane copolymer.

Among these nonionic surfactants, from the viewpoint of non-friction feeling and the moist feeling after cleansing, polyoxyethylene alkyl ethers are preferable.

The surfactant as the component (B) can be used in a single kind or two or more kinds in combination, and the content thereof in the skin cleansing agent is, from the viewpoint of the cleansing property and the skin feeling during and after cleansing, preferably 0.01 mass % or more, more preferably 0.05 mass % or more, and further more preferably 0.1 mass % or more and is preferably 30 mass % or less, more preferably 20 mass % or less, and further more preferably 10 mass % or less. The content of the component (B) in the skin cleansing agent is preferably from 0.01 to 30 mass %, more preferably from 0.05 to 20 mass %, and further more preferably from 0.1 to 10 mass %.

In order to further improve the cleansing ability, the content of the component (B) in the skin cleansing agent is preferably from 3.5 to 10 mass %. On the other hand, from the viewpoint of further reducing the friction feeling after cleansing and further retaining the softness of the skin, the content of the component (B) in the skin cleansing agent is preferably 0.1 mass % or more and less than 3.5 mass %.

In the present invention, the content of water as the component (C) determines the salt concentration which affects the stability of the component (A), and the content in the skin cleansing agent is, from the viewpoint of the stability of the (A) and the solubility of the components other than the (A) in the skin cleansing agent, preferably 1 mass % or more, more preferably 5 mass % or more, and further more preferably 10 mass % or more and is preferably 90 mass % or less, more preferably 70 mass % or less, and further more preferably 60 mass % or less. The content of water as the component (C) in the skin cleansing agent is preferably from 1 to 90 mass %, more preferably from 5 to 70 mass %, and further more preferably from 10 to 60 mass %.

The skin cleansing agent of the present invention preferably further contains (D) one or more selected from the group consisting of 2-amino-2-hydroxymethyl-1,3-propanediol (tromethamine), 2-amino-2-methyl-1-propanol, 2-amino-2-methyl-1,3-propanediol, and arginine, more preferably one or more selected from the group consisting of tromethamine and arginine, from the viewpoint of improving the sebum cleansing property, the fresh feeling after cleansing, and adjusting the salt concentration of the skin cleansing agent.

In the present invention, when the component (D) is contained, since sebum can be removed without changing feelings, such as the friction feeling, the moist feeling, and the softness of the skin, even if the content of the component (B) is decreased (e.g., when the content of the component (B) is less than 3.5 mass %) for reducing the friction feeling after cleansing and placing emphasis on the moisturizing effect and the softness of the skin, it is preferable to contain the component (D) from the viewpoint of capable of achieving the same level of the sebum cleansing ability as when the surfactant is contained at a high concentration and simultaneously achieving high moisture retaining ability, suppression of friction feeling, and feelings such as the softness of the skin.

The content of the component (D) in the skin cleansing agent is, from the viewpoint of improving the sebum cleansing property, the fresh feeling after cleansing, and adjusting the salt concentration of the skin cleansing agent, preferably 0.1 mass % or more, more preferably 1 mass % or more, and further more preferably 3 mass % or more and preferably 30 mass % or less, more preferably 20 mass % or less, and further more preferably 12 mass % or less. In addition, the content of the component (D) in the skin cleansing agent is preferably from 0.1 to 30 mass %, more preferably from 1 to 20 mass %, and further more preferably from 3 to 12 mass %.

The skin cleansing agent of the present invention can include, in addition to the above-described components, components which are used in general cleansing agent compositions within a range that does not impair the effects of the present invention. Examples thereof include lower alcohols, such as ethanol and isopropyl alcohol; aromatic alcohols, such as benzyl alcohol and benzyloxy ethanol; cellosolves, such as ethyl cellosolve and butyl cellosolve; carbitols, such as ethyl carbitol and butyl carbitol; moisturizing components, such as sugar (derivatives), amino acid (derivatives), animal and plant (protein) derivatives, and animal and plant extracts; silicone derivatives, such as polyoxyalkylene-modified silicone; inorganic or organic salts, such as sodium sulfate, sodium carbonate, sodium hydrogen carbonate, potassium chloride, sodium chloride, and sodium citrate; pH adjusters, such as an acid and an alkali; anti-inflammatory agents, such as glycyrrhetic acid, glycyrrhizic acid, and derivatives thereof; bactericides, such as isopropylmethylphenol; preservatives, sequestering agents, antioxidants, UV absorbers, anionic polymers, nonionic polymers, amphoteric polymers, fragrances, thickeners, vitamins, natural pigments, and colorants other than the above, such as tar pigments.

In the skin cleansing agent of the present invention, from the viewpoint of the stability of the (A) and skin irritation, the salt content in the skin cleansing agent based on the content of water is preferably 2 mass % or more, more preferably 5 mass % or more, and further more preferably 7 mass % or more and is preferably 70 mass % or less, more preferably 50 mass % or less, further more preferably 35 mass % or less, and even more preferably 30 mass % or less. In addition, in the skin cleansing agent of the present invention, the salt content in the skin cleansing agent based on the content of water, i.e., the salt concentration, is preferably from 2 to 70 mass %, more preferably from 5 to 50 mass %, further more preferably from 7 to 35 mass %, and even more preferably from 7 to 30 mass %.

In the skin cleansing agent of the present invention, the salt concentration refers to the salt concentration with respect to water of the component (C). Examples of the salts include an anionic surfactant, the component (D), and a chelating agent.

The skin cleansing agent of the present invention can be manufactured by a general method and includes water as the component (C) to be a water-based skin cleansing agent. The skin cleansing agent can be in, for example, a liquid, cream, gel, or solid soap form.

The skin cleansing agent of the present invention is used for skin cleansing and is more preferably used as hand soap, facial cleanser, or body soap.

The skin cleansing agent of the present invention can cleanse the skin by, for example, being applied to the skin and then being rinsed with water. In cleansing of the face, it is preferable to lightly wet the entire face and the hands with water and then apply the agent to the entire face.

The present invention further discloses the following compositions relating to the above-described embodiments.

<1> A skin cleansing agent containing the following components (A), (B), and (C):
a particle (A) including (A1), (A2), and (A3):
  a water-holding oil agent (A1) in an amount of from 0.0001 to 13 mass % in the skin cleansing agent;
  a moisturizing agent (A2) in an amount of from 0.001 to 25 mass % in the skin cleansing agent; and
  a polymer (A3);
a surfactant (B); and
water (C).

<2> The skin cleansing agent according to the <1>, wherein the (A1) is an oil agent which can hold water equal to or more than its own weight at 50° C.

<3> The skin cleansing agent according to the <1> or <2>, wherein the (A1) preferably includes one or more selected from the group consisting of a dimer acid ester, a glycerol fatty acid ester, a pentaerythritol fatty acid ester, a fatty acid cholesterol ester having from 16 to 22 carbon atoms, a phytosterol ester having from 16 to 22 carbon atoms, and an N-acyl amino acid ester.

<4> The skin cleansing agent according to any one of the <1> to <3>, wherein the (A1) preferably includes one or more selected from the group consisting of a pentaerythritol fatty acid ester, a fatty acid cholesterol ester having from 16 to 22 carbon atoms, and an N-acyl amino acid ester, more preferably includes one or more selected from the group consisting of dipentaerythrityl tripolyhydroxystearate, cholesteryl hydroxystearate, phytosteryl/decyltetradecyl N-myristoyl-N-methylalanine, and di(cholesteryl/behenyl/octyldodecyl) N-lauroyl-L-glutamate, and further more preferably includes dipentaerythrityl tripolyhydroxystearate.

<5> The skin cleansing agent according to any one of the <1> to <4>, wherein the (A2) preferably includes one or more selected from oily moisturizing agents.

<6> The skin cleansing agent according to any one of the <1> to <5>, wherein the (A2) preferably includes an oily moisturizing agent and more preferably includes one or more selected from the group consisting of a hydrocarbon oil, an ester oil other than the (A1), and a higher alcohol having 10 or more carbon atoms.

<7> The skin cleansing agent according to any one of the <1> to <6>, wherein the (A2) preferably includes one or more selected from the group consisting of squalane and petrolatum and more preferably includes squalane and petrolatum.

<8> The skin cleansing agent according to any one of the <1> to <7>, wherein the (A2) preferably includes one or more selected from water-soluble moisturizing agents.

<9> The skin cleansing agent according to any one of the <1> to <8>, wherein the (A2) preferably includes one or more selected from the group consisting of a divalent alcohol, a tri- or higher valent alcohol, a sugar, and a sugar alcohol and more preferably includes glycerol.

<10> The skin cleansing agent according to any one of the <1> to <9>, wherein the (A2) preferably includes one or more selected from the group consisting of squalane, petrolatum, liquid paraffin, isostearyl isostearate, neopentyl glycol dicaprate, jojoba oil, and glycerol.

<11> The skin cleansing agent according to any one of the <1> to <10>, wherein the (A1) and the (A2) are preferably disposed inside the particle of the component (A).

<12> The skin cleansing agent according to any one of the <1> to <11>, wherein the (A3) is preferably a hydrophilic polymer.

<13> The skin cleansing agent according to any one of the <1> to <12>, wherein the (A3) is preferably a salt-sensitive polymer.

<14> The skin cleansing agent according to any one of the <1> to <13>, wherein the (A3) is preferably an acid-modified polyvinyl alcohol and more preferably includes an acid-modified polyvinyl alcohol having introduced therein one or more selected from the group consisting of a sulfonic acid group and a carboxylic acid group.

<15> The skin cleansing agent according to any one of the <1> to <14>, wherein the (A3) is preferably a carboxylic acid-modified polyvinyl alcohol.

<16> The skin cleansing agent according to the <14> or <15>, wherein the (A3) preferably has an acid modification rate of from 0.1 to 10 mol %, more preferably from 0.5 to 5 mol %, and further more preferably from 1 to 3 mol %.

<17> The skin cleansing agent according to any one of the <14> to <16>, wherein a content of the acid-modified polyvinyl alcohol in the particle of the component (A) is preferably from 1 to 99 mass %, more preferably from 5 to 95 mass %, further more preferably from 10 to 90 mass %, even more preferably from 20 to 85 mass %, and further more preferably from 40 to 80 mass %.

<18> The skin cleansing agent according to any one of the <14> to <17>, wherein the acid-modified polyvinyl alcohol preferably has a molecular weight of from 5 000 to 1 000 000, more preferably from 10 000 to 500 000, further more preferably from 30 000 to 200 000, and even more preferably from 50 000 to 200 000.

<19> The skin cleansing agent according to any one of the <14> to <18>, wherein a mass ratio of the content of the acid-modified polyvinyl alcohol to a content of the components (A1) and (A2), (acid-modified polyvinyl alcohol/the components (A1) and (A2)), in the component (A) is preferably from 0.1 to 90, more preferably from 0.3 to 70, further more preferably from 0.5 to 50, even more preferably from 0.7 to 30, and further more preferably from 1 to 10.

<20> The skin cleansing agent according to any one of the <1> to <19>, wherein the particle of the component (A) is preferably manufactured by removing water from an emulsified composition prepared by emulsification of the (A3) and the oil phase including the (A1) and the (A2).

<21> The skin cleansing agent according to any one of the <1> to <20>, wherein the particle of the component (A) preferably has an average particle diameter of from 1 to 1 500 μm, more preferably from 5 to 1 000 μm, further more preferably from 10 to 500 μm, even more preferably from 20 to 200 μm, and further more preferably from 30 to 100 μm.

<22> The skin cleansing agent according to any one of the <1> to <21>, wherein a content of the component (A) in the skin cleansing agent is preferably from 0.001 to 50 mass %, more preferably from 0.01 to 20 mass %, and further more preferably from 0.1 to 10 mass %.

<23> The skin cleansing agent according to any one of the <1> to <22>, wherein a content of the component (B) in the skin cleansing agent is preferably from 0.01 to 30 mass %, more preferably from 0.05 to 20 mass %, and further more preferably from 0.1 to 10 mass %.

<24> The skin cleansing agent according to any one of the <1> to <23>, wherein a content of the component (C) in the skin cleansing agent is preferably from 1 to 90 mass %, more preferably from 5 to 70 mass %, and further more preferably from 10 to 60 mass %.

<25> The skin cleansing agent according to any one of the <1> to <24>, preferably further containing (D) one or more selected from the group consisting of 2-amino-2-hydroxymethyl-1,3-propanediol, 2-amino-2-methyl-1-propanol, 2-amino-2-methyl-1,3-propanediol, and arginine.

<26> The skin cleansing agent according to the <25>, wherein a content of the component (D) in the skin cleansing agent is preferably from 0.1 to 30 mass %, more preferably from 1 to 20 mass %, and further more preferably from 3 to 12 mass %.

<27> The skin cleansing agent according to any one of the <1> to <26>, wherein, preferably, a content of the (A1) in the skin cleansing agent is from 0.001 to 5 mass %, and a content of the (A2) in the skin cleansing agent is from 0.01 to 10 mass %.

<28> The skin cleansing agent according to any one of the <1> to <27>, wherein the mass ratio of the (A1) to the (A2), (A1)/(A2), is preferably from 0.004 to 60, more preferably from 0.005 to 50, further more preferably from 0.01 to 30, even more preferably from 0.05 to 20, and even more preferably from 0.15 to 1.

<29> The skin cleansing agent according to any one of the <1> to <28>, wherein a salt content in the skin cleansing agent based on the content of water is from 2 to 70 mass %, more preferably from 5 to 50 mass %, and further more preferably from 7 to 30 mass %.

<30> The skin cleansing agent according to any one of the <1> to <29>, wherein the content of the component (B) in the skin cleansing agent is preferably from 3.5 to 10 mass %.

<31> The skin cleansing agent according to any one of the <1> to <30>, wherein, preferably, the content of the component (B) is 0.1 mass % or more and less than 3.5 mass % and the content of the component (D) is from 1 to 20 mass %, in the skin cleansing agent.

<32> A method for cleansing a skin, including applying the skin cleansing agent according to any one of the <1> to <31> to the skin, and then rinsing with water.

EXAMPLES

Test Example 1: Validation of Salt Sensitivity of (A3)

A thin film sheet of a polymer ((maleic acid/vinyl alcohol) copolymer Na) used as component (A3) in examples was produced by the following method.

That is, GOHSENX T-330H (PVA, 22 g) was added to deionized water (78 g) and was dissolved at 80° C. for 60 minutes to prepare a 22% aqueous PVA solution. The 22% PVA aqueous solution (5 g) was applied on a glass substrate with a dropping pipette. The aqueous PVA solution was applied on the glass substrate so as to form a liquid film having a length of 20 cm by using an applicator (manufactured by Taiyu Kizai Co., Ltd., Model 3F-7721T, film thickness: 250 μm, width: 29 mm). The liquid film on the glass substrate was dried at 100° C. for 60 minutes. The resulting dried product was peeled off from the glass substrate to obtain a thin film sheet of a PVA film. The sheet thickness after drying was 46 μm.

The resulting thin film sheet was cut into a 2 cm square with a cutter and was quietly immersed in a 100-mL beaker containing 50 g of a 1 mass % saline solution. While stirring the beaker with a stirrer of 2.0 cm, mixing was performed at room temperature (25° C.) for 5 minutes, and then whether the sheet was dissolved or not was visually evaluated. Regarding the solubility of a thin film sheet of acid-modified polyvinyl alcohol in a 10 mass % saline solution, the method above was performed by using a 10 mass % saline solution.

As a result, while the thin film sheet immersed in a 1 mass % saline solution was completed dissolved, the thin film sheet immersed in a 10 mass % saline solution was not dissolved. It was confirmed to be salt sensitive.

Examples 1 to 36 and Comparative Examples 1 to 5

Skin cleansing agents of the compositions shown in Tables 2 to 6 were manufactured and were evaluated for the sebum cleansing ability, skin feelings (rinsability, non-friction feeling, persistence of moist feeling, persistence of non-stretched feeling, and persistence of softness) after cleansing, and the storage stability.

The particles of the component (A) shown in the tables (upper stage) were manufactured by the method shown in Manufacturing Examples 1 to 26.

Manufacturing Example 1 (Manufacturing of Components (A) Used in Examples 1 and 9 to 21 and Comparative Example 5)

A (maleic acid/vinyl alcohol) copolymer Na (GOHSENX T-330H, manufactured by Mitsubishi Chemical Corporation, 14.01 kg) was added to and mixed with deionized water (76.59 kg) with heating at 80° C., followed by cooling to 75° C. to prepare a water phase. Dipentaerythrityl tripolyhydroxystearate (manufactured by The Nisshin OilliO Group, Ltd., Salacos WO-6, 1.71 kg), petrolatum (manufactured by Sonneborn LLC, Super White Protopet, 1.71 kg), squalane (manufactured by Nippon Surfactant Industries Co., Ltd., NIKKOL Squalane, 3.43 kg), polyoxyethylene (20EO) sorbitan monostearate (nonionic surfactant, manufactured by Kao Corporation, Rheodol TW-S120V, 1.54 kg), and sorbitan stearate (nonionic surfactant, manufactured by Kao Corporation, Rheodol SP-S10V, 0.51 kg) were mixed while heating at 75° C. to prepare an oil phase. The oil phase was added to the prepared water phase, and stirring was performed by using an anchor stirring blade, and at the same time, while circulating the mixture phase, a dispersion procedure of the circulating fluid was performed by using a milder. Subsequently, an appropriate amount of water was added thereto to prepare an emulsion. The emulsion obtained by the above emulsification procedure was spray dried by using a spray drier to obtain particles of the component (A). The composition of the component (A) finally obtained by spray drying is shown in the tables. The resulting particles had an average dried particle diameter of 81 μm.

Manufacturing Example 2 (Manufacturing of Component (A) Used in Example 2)

A particle of the component (A) was manufactured by the same method as in Manufacturing Example 1 except that the component (A1) was replaced with cholesteryl hydroxystearate.

Manufacturing Example 3 (Manufacturing of Component (A) Used in Example 3)

A particle of the component (A) was manufactured by the same method as in Manufacturing Example 1 except that the component (A2) was replaced with petrolatum (5.14 kg).

Manufacturing Example 4 (Manufacturing of Component (A) Used in Example 4)

A particle of the component (A) was manufactured by the same method as in Manufacturing Example 1 except that the component (A2) was replaced with petrolatum (0.91 kg) and squalane (4.23 kg).

Manufacturing Example 5 (Manufacturing of Component (A) Used in Example 5)

A particle of the component (A) was manufactured by the same method as in Manufacturing Example 1 except that the component (A2) was replaced with squalane (5.14 kg).

Manufacturing Example 6 (Manufacturing of Component (A) Used in Example 6)

A particle of the component (A) was manufactured by the same method as in Manufacturing Example 1 except that the component (A2) was replaced with glycerol (manufactured by Kao Corporation, concentrated glycerol for cosmetics, 5.14 kg).

Manufacturing Example 7 (Manufacturing of Component (A) Used in Example 7)

A particle of the component (A) was manufactured by the same method as in Manufacturing Example 1 except that the component (A1) was replaced with dipentaerythrityl tripolyhydroxystearate (6.16 kg) and that the component (A2) was replaced with petrolatum (0.68 kg).

Manufacturing Example 8 (Manufacturing of Component (A) Used in Example 8)

A particle of the component (A) was manufactured by the same method as in Manufacturing Example 1 except that the component (A1) was replaced with dipentaerythrityl tripolyhydroxystearate (0.684 kg) and that the component (A2) was replaced with petrolatum (6.16 kg).

Manufacturing Example 9 (Manufacturing of Particle Used in Comparative Example 1)

A particle was manufactured by the same method as in Manufacturing Example 1 except that the component (A1) was not used and that the component (A2) was replaced with petrolatum (6.84 kg).

Manufacturing Example 10 (Manufacturing of Particle Used in Comparative Example 2)

A particle was manufactured by the same method as in Manufacturing Example 1 except that the component (A1) was replaced with dipentaerythrityl tripolyhydroxystearate (6.84 kg) and that the component (A2) was not used.

Manufacturing Example 11 (Manufacturing of Particle Used in Comparative Example 3)

A particle was manufactured by the same method as in Manufacturing Example 1 except that the components (A1) and (A2) were not used.

Manufacturing Example 12 (Manufacturing of Component (A) Used in Example 22)

A particle of the component (A) was manufactured by the same method as in Manufacturing Example 1 except that the component (A1) was replaced with phytosteryl/decyltetradecyl myristoylmethyl-β-alanine (manufactured by Ajinomoto Co., Ltd., Eldew APS-307).

Manufacturing Example 13 (Manufacturing of Component (A) Used in Example 23)

A particle of the component (A) was manufactured by the same method as in Manufacturing Example 1 except that the component (A1) was replaced with di(cholesteryl/behenyl/octyldodecyl) lauroyl glutamate (manufactured by Ajinomoto Co., Ltd., Eldew CL-301).

Manufacturing Example 14 (Manufacturing of Component (A) Used in Example 24)

A particle of the component (A) was manufactured by the same method as in Manufacturing Example 1 except that the component (A2) was replaced with liquid paraffin (manufactured by NOF Corporation, Parleam EX, 5.14 kg).

Manufacturing Example 15 (Manufacturing of Component (A) Used in Example 25)

A particle of the component (A) was manufactured by the same method as in Manufacturing Example 1 except that the component (A2) was replaced with isostearyl isostearate (manufactured by Kokyu Alcohol Kogyo Co., Ltd., ISIS, 5.14 kg).

Manufacturing Example 16 (Manufacturing of Component (A) Used in Example 26)

A particle of the component (A) was manufactured by the same method as in Manufacturing Example 1 except that the component (A2) was replaced with neopentyl glycol dicaprate (manufactured by The Nisshin OilliO Group, Ltd., Estemol N-01, 5.14 kg).

Manufacturing Example 17 (Manufacturing of Component (A) Used in Example 27)

A particle of the component (A) was manufactured by the same method as in Manufacturing Example 1 except that the component (A2) was replaced with jojoba oil (manufactured by Koei Kogyo Co., Ltd., Purified Jojoba Oil, 5.14 kg).

Manufacturing Example 18 (Manufacturing of Component (A) Used in Example 28)

A particle of the component (A) was manufactured by the same method as in Manufacturing Example 1 except that the component (A1) was replaced with dipentaerythrityl tripolyhydroxystearate (3.11 kg) and that the component (A2) was replaced with petrolatum (3.74 kg).

Manufacturing Example 19 (Manufacturing of Component (A) Used in Example 29)

A particle of the component (A) was manufactured by the same method as in Manufacturing Example 1 except that the component (A1) was replaced with dipentaerythrityl tripolyhydroxystearate (6.72 kg) and that the component (A2) was replaced with petrolatum (0.13 kg).

Manufacturing Example 20 (Manufacturing of Component (A) Used in Example 30)

A particle of the component (A) was manufactured by the same method as in Manufacturing Example 1 except that the component (A1) was replaced with dipentaerythrityl tripolyhydroxystearate (6.52 kg) and that the component (A2) was replaced with petrolatum (0.33 kg).

Manufacturing Example 21 (Manufacturing of Component (A) Used in Example 31)

A particle of the component (A) was manufactured by the same method as in Manufacturing Example 1 except that the component (A1) was replaced with dipentaerythrityl tripolyhydroxystearate (3.43 kg) and that the component (A2) was replaced with petrolatum (3.43 kg).

Manufacturing Example 22 (Manufacturing of Component (A) Used in Example 32)

A particle of the component (A) was manufactured by the same method as in Manufacturing Example 1 except that the component (A1) was replaced with dipentaerythrityl tripolyhydroxystearate (6.63 kg) and that the component (A2) was replaced with petrolatum (0.22 kg).

Manufacturing Example 23 (Manufacturing of Component (A) Used in Example 33)

A particle of the component (A) was manufactured by the same method as in Manufacturing Example 1 except that the component (A1) was replaced with dipentaerythrityl tripolyhydroxystearate (1.14 kg) and the component (A2) was replaced with petrolatum (5.71 kg).

Manufacturing Example 24 (Manufacturing of Component (A) Used in Example 34)

A particle of the component (A) was manufactured by the same method as in Manufacturing Example 1 except that the component (A1) was replaced with dipentaerythrityl tripolyhydroxystearate (0.33 kg) and the component (A2) was replaced with petrolatum (6.52 kg).

Manufacturing Example 25 (Manufacturing of Component (A) Used in Example 35)

A particle of the component (A) was manufactured by the same method as in Manufacturing Example 1 except that the component (A1) was replaced with dipentaerythrityl tripolyhydroxystearate (0.03 kg) and the component (A2) was replaced with petrolatum (6.82 kg).

Manufacturing Example 26 (Manufacturing of Component (A) Used in Example 36)

A particle of the component (A) was manufactured by the same method as in Manufacturing Example 1 except that the component (A1) was replaced with dipentaerythrityl tripolyhydroxystearate (0.07 kg) and the component (A2) was replaced with petrolatum (6.78 kg).

(Manufacturing Method)

(1) Examples 1 to 17 and 19 to 36 and Comparative Examples 1 to 3

Components (B), (C), and (D) and remaining components other than the component (A) were mixed while heating at 50° C. and then cooled. The component (A) was added thereto after the temperature fell to 40° C. or less to manufacture a skin cleansing agent.

(2) Example 18 and Comparative Example 5

Components (B) and (C) and remaining components other than the component (A) were mixed while heating at 50° C. and then cooled. The component (A) was added thereto after the temperature fell to 40° C. or less to manufacture a skin cleansing agent.

(3) Comparative Example 4

Components (A1), (A2), (B), (C), and (D) and remaining components were mixed while heating at 50° C. and then cooled to manufacture a skin cleansing agent.

(Evaluation Method)
(1) Sebum Cleansing Ability

A circle with a diameter of 3 cm was drawn on the medial side of the human forearm, and the color (reference color) was measured by using a spectral colorimeter (manufactured Konica Minolta, CM-600d). Subsequently, model comedo sebum (20 μg) with the following composition produced by dispersing carbon black was applied, and the color difference after drying for 30 minutes, ΔEa, was measured by using a spectral colorimeter. Each skin cleansing agent (1 g) was dropped to the application site, and massage cleansing was performed for 30 seconds. Rinsing with tap water (40 mL) and air drying were performed. After the drying, the color difference after cleansing, ΔEb, was measured by using a spectral colorimeter. The cleansing rate was evaluated on a 4-point scale based on the cleansing rate E obtained by the following expression.

<Calculation Expression of Cleansing Rate E (%)>

Cleansing rate $E$ (%)=(1−(color difference $\Delta Eb$ after cleansing/color difference $\Delta Ea$ before cleansing))×100

4: the cleansing rate E is 75% or more,
3: the cleansing rate E is 60% or more and less than 75%,
2: the cleansing rate E is 45% or more and less than 60%, and
1: the cleansing rate E is less than 45%.

TABLE 1

|  | Component | (parts by mass) |
|---|---|---|
| Model comedo sebum | Squalene | 7.9 |
|  | Myristyl myristate | 13.9 |
|  | Triglyceride | 7.1 |
|  | Cholesterol | 11.9 |
|  | Cholesterol ester | 4 |
|  | Lauric acid | 0.8 |
|  | Myristic acid | 6.3 |
|  | Palmitic acid | 24.6 |
|  | Stearic acid | 4.8 |
|  | Oleic acid | 18.7 |
| Cleansing marker | Carbon black | 5 |

(2) Skin Feeling after Cleansing

The entire face and the hands were lightly wetted, and each skin cleansing agent (2 g) was lightly spread on the entire face and was then rinsed with tap water.

The rinsability was sensorily evaluated according to the 4-point scale criteria shown below in 0.5 increments based on the speed of disappearing of the sliminess of the skin sensed with the hands during rinsing. In addition, non-friction feeling during rinsing was sensorily evaluated according to the 4-point scale criteria shown below in 0.5 increments.

After rinsing, towel drying was performed. Persistence of moist feeling, persistence of non-stretched feeling, and persistence of softness after 10 minutes from the towel drying were sensorily evaluated according to the 4-point scale criteria shown below in 0.5 increments.

These evaluations were performed by two special panelists, and the results are shown by the average value of the evaluations of the two panelists.

<Evaluation Criteria of Rinsability>
4: the rinsability is good,
3: the rinsability is slightly good,
2: the rinsability is not good, and
1: the rinsability is poor.

<Evaluation Criteria of Non-Friction Feeling>
4: dry and smooth feeling is obtained,
3: dry and smooth feeling is slightly obtained,
2: creaking and sticking are slightly felt, and
1: creaking and sticking are felt.

<Evaluation Criteria of Persistence of Moist Feeling>
4: moist feeling is maintained,
3: moist feeling is slightly maintained,
2: moist feeling is not maintained too long, and
1: moist feeling is not maintained.

<Evaluation Criteria of Persistence of Non-Stretched Feeling>
4: non-stretched feeling is maintained,
3: non-stretched feeling is slightly maintained,
2: slightly stretched feeling occurs over time, and
1: stretched feeling occurs after a while.

<Evaluation Criteria of Persistence of Softness>
4: softness is maintained,
3: softness is slightly maintained,
2: softness is not maintained too long, and
1: softness is not maintained.

(3) Storage Stability

The appearance (separation of moisturizing agent) of each skin cleansing agent after leaving to stand at room temperature for 24 hours was visually validated and evaluated by the following criteria.

2: the moisturizing agent is not separated, and
1: the moisturizing agent is separated.

TABLE 2

|  |  |  | Example 1 | Example 2 | Example 3 | Example 4 | Example 5 | Example 6 | Example 7 | Example 8 |
|---|---|---|---|---|---|---|---|---|---|---|
| A | A1 | Dipentaerythrityl tripolyhydroxystearate | 7.5 |  | 7.5 | 7.5 | 7.5 | 7.5 | 27.0 | 3.0 |
|  |  | Cholesteryl hydroxystearate |  | 7.5 |  |  |  |  |  |  |
|  | A2 | Squalane | 15.0 | 15.0 |  | 18.5 | 22.5 |  | 0 | 0 |
|  |  | Petrolatum | 7.5 | 7.5 | 22.5 | 4.0 |  |  | 3 | 27 |
|  |  | Glycerol |  |  |  |  |  | 22.5 |  |  |
|  | A3 | Sodium (maleic acid/vinyl alcohol) copolymer* | 59.4 | 59.4 | 59.4 | 59.4 | 59.4 | 59.4 | 59.4 | 59.4 |
|  | Others | Polyoxyethylene (20EO) sorbitan monostearate | 6.8 | 6.8 | 6.8 | 6.8 | 6.8 | 6.8 | 6.8 | 6.8 |
|  |  | Sorbitan stearate | 2.3 | 2.3 | 2.3 | 2.3 | 2.3 | 2.3 | 2.3 | 2.3 |
|  |  | Water | 1.5 | 1.5 | 1.5 | 1.5 | 1.5 | 1.5 | 1.5 | 1.5 |
| Total |  |  | 100.0 | 100.0 | 100.0 | 100.0 | 100.0 | 100.0 | 100.0 | 100.0 |
| Amount to be added to skin cleansing agent |  |  | 2 | 2 | 2 | 2 | 2 | 2 | 2 | 2 |
| A | A1 | Dipentaerythrityl tripolyhydroxystearate | 0.15 | 0.00 | 0.15 | 0.15 | 0.15 | 0.15 | 0.54 | 0.06 |
|  |  | Cholesteryl hydroxystearate | 0.00 | 0.15 | 0.00 | 0.00 | 0.00 | 0.00 | 0.00 | 0.00 |
|  | A2 | Squalane | 0.30 | 0.30 | 0.00 | 0.37 | 0.45 | 0.00 | 0.00 | 0.00 |
|  |  | Petrolatum | 0.15 | 0.15 | 0.45 | 0.08 | 0.00 | 0.00 | 0.06 | 0.54 |
|  |  | Glycerol | 0.00 | 0.00 | 0.00 | 0.00 | 0.00 | 0.45 | 0.00 | 0.00 |
|  | A3 | Sodium (maleic acid/vinyl alcohol) copolymer* | 1.19 | 1.19 | 1.19 | 1.19 | 1.19 | 1.19 | 1.19 | 1.19 |
|  | Others | Polyoxyethylene (20EO) sorbitan monostearate | 0.14 | 0.14 | 0.14 | 0.14 | 0.14 | 0.14 | 0.14 | 0.14 |
|  |  | Sorbitan stearate | 0.05 | 0.05 | 0.05 | 0.05 | 0.05 | 0.05 | 0.05 | 0.05 |
|  |  | Water | 0.03 | 0.03 | 0.03 | 0.03 | 0.03 | 0.03 | 0.03 | 0.03 |
| B |  | Steareth-13 | 0.20 | 0.20 | 0.20 | 0.20 | 0.20 | 0.20 | 0.20 | 0.20 |
|  |  | Laureth-21 | 0.20 | 0.20 | 0.20 | 0.20 | 0.20 | 0.20 | 0.20 | 0.20 |
|  |  | Sodium lauroyl glutamate | 0.00 | 0.00 | 0.00 | 0.00 | 0.00 | 0.00 | 0.00 | 0.00 |
| C |  | Water | 48.05 | 48.05 | 48.05 | 48.05 | 48.05 | 48.05 | 48.05 | 48.05 |
| D |  | Tromethamine | 5.00 | 5.00 | 5.00 | 5.00 | 5.00 | 5.00 | 5.00 | 5.00 |
| Others |  | Sorbitol | 21.00 | 21.00 | 21.00 | 21.00 | 21.00 | 21.00 | 21.00 | 21.00 |
|  |  | Trehalose | 7.00 | 7.00 | 7.00 | 7.00 | 7.00 | 7.00 | 7.00 | 7.00 |

TABLE 2-continued

|  |  | Example 1 | Example 2 | Example 3 | Example 4 | Example 5 | Example 6 | Example 7 | Example 8 |
|---|---|---|---|---|---|---|---|---|---|
|  | Glycerol | 7.00 | 7.00 | 7.00 | 7.00 | 7.00 | 7.00 | 7.00 | 7.00 |
|  | PG | 5.00 | 5.00 | 5.00 | 5.00 | 5.00 | 5.00 | 5.00 | 5.00 |
|  | Mannitol | 4.00 | 4.00 | 4.00 | 4.00 | 4.00 | 4.00 | 4.00 | 4.00 |
|  | Acrylates/C10-30 alkyl acrylate crosspolymer | 0.17 | 0.17 | 0.17 | 0.17 | 0.17 | 0.17 | 0.17 | 0.17 |
|  | Phenoxyethanol | 0.20 | 0.20 | 0.20 | 0.20 | 0.20 | 0.20 | 0.20 | 0.20 |
|  | EDTA-2Na | 0.10 | 0.10 | 0.10 | 0.10 | 0.10 | 0.10 | 0.10 | 0.10 |
|  | Fragrance | 0.08 | 0.08 | 0.08 | 0.08 | 0.08 | 0.08 | 0.08 | 0.08 |
| Total |  | 100 | 100 | 100 | 100 | 100 | 100 | 100 | 100 |
| (A1) mass % in skin cleansing agent |  | 0.15 | 0.15 | 0.15 | 0.15 | 0.15 | 0.15 | 0.54 | 0.06 |
| (A2) mass % in skin cleansing agent |  | 0.45 | 0.45 | 0.45 | 0.45 | 0.45 | 0.45 | 0.06 | 0.54 |
| A1/A2 |  | 0.33 | 0.33 | 0.33 | 0.33 | 0.33 | 0.33 | 9.00 | 0.11 |
| Salt concentration (salt concentration with respect to water (C)) |  | 10.6 | 10.6 | 10.6 | 10.6 | 10.6 | 10.6 | 10.6 | 10.6 |
| Evaluation | Sebum cleansing ability | 4 | 4 | 4 | 4 | 4 | 4 | 4 | 4 |
|  | Rinsability | 4 | 4 | 4 | 4 | 4 | 4 | 4 | 3.75 |
|  | Non-friction feeling | 4 | 4 | 4 | 4 | 4 | 3.5 | 3.5 | 3.75 |
|  | Persistence of moist feeling | 4 | 4 | 4 | 3.75 | 3.5 | 3 | 3.75 | 3.5 |
|  | Persistence of non-stretched feeling | 4 | 4 | 3.5 | 4 | 4 | 3 | 3.75 | 3.5 |
|  | Persistence of softness | 4 | 3.75 | 3.75 | 4 | 4 | 3.5 | 3.5 | 3.75 |
|  | Storage stability | 2 | 2 | 2 | 2 | 2 | 2 | 2 | 2 |

*GOHSENX T-330H, manufactured by Mitsubishi Chemical Corporation

TABLE 3

|  |  |  | Example 9 | Example 10 | Example 11 | Example 12 | Example 13 | Example 14 | Example 15 |
|---|---|---|---|---|---|---|---|---|---|
| A | A1 | Dipentaerythrityl tripolyhydroxystearate | 7.5 | 7.5 | 7.5 | 7.5 | 7.5 | 7.5 | 7.5 |
|  |  | Cholesteryl hydroxystearate |  |  |  |  |  |  |  |
|  | A2 | Squalane | 15.0 | 15.0 | 15.0 | 15.0 | 15.0 | 15.0 | 15.0 |
|  |  | Petrolatum | 7.5 | 7.5 | 7.5 | 7.5 | 7.5 | 7.5 | 7.5 |
|  |  | Glycerol |  |  |  |  |  |  |  |
|  | A3 | Sodium (maleic acid/vinyl alcohol) copolymer* | 59.4 | 59.4 | 59.4 | 59.4 | 59.4 | 59.4 | 59.4 |
|  | Others | Polyoxyethylene (20EO) sorbitan monostearate | 6.8 | 6.8 | 6.8 | 6.8 | 6.8 | 6.8 | 6.8 |
|  |  | Sorbitan stearate | 2.3 | 2.3 | 2.3 | 2.3 | 2.3 | 2.3 | 2.3 |
|  |  | Water | 1.5 | 1.5 | 1.5 | 1.5 | 1.5 | 1.5 | 1.5 |
| Total |  |  | 100.0 | 100.0 | 100.0 | 100.0 | 100.0 | 100.0 | 100.0 |
| Amount to be added to skin cleansing agent |  |  | 0.01 | 0.1 | 0.5 | 1 | 4 | 8 | 16 |
| A | A1 | Dipentaerythrityl tripolyhydroxystearate | 0.0008 | 0.01 | 0.04 | 0.08 | 0.29 | 0.57 | 1.05 |
|  |  | Cholesteryl hydroxystearate | 0.00 | 0.00 | 0.00 | 0.00 | 0.00 | 0.00 | 0.00 |
|  | A2 | Squalane | 0.0015 | 0.02 | 0.08 | 0.15 | 0.59 | 1.13 | 2.11 |
|  |  | Petrolatum | 0.0008 | 0.01 | 0.04 | 0.08 | 0.29 | 0.57 | 1.05 |
|  |  | Glycerol | 0.00 | 0.00 | 0.00 | 0.00 | 0.00 | 0.00 | 0.00 |
|  | A3 | Sodium (maleic acid/vinyl alcohol) copolymer* | 0.0061 | 0.06 | 0.30 | 0.60 | 2.33 | 4.48 | 8.34 |
|  | Others | Polyoxyethylene (20EO) sorbitan monostearate | 0.0007 | 0.01 | 0.03 | 0.07 | 0.27 | 0.51 | 0.95 |
|  |  | Sorbitan stearate | 0.0002 | 0.00 | 0.01 | 0.02 | 0.09 | 0.17 | 0.32 |
|  |  | Water | 0.0002 | 0.00 | 0.01 | 0.02 | 0.06 | 0.11 | 0.21 |
| B |  | Steareth-13 | 0.20 | 0.20 | 0.20 | 0.20 | 0.20 | 0.19 | 0.18 |
|  |  | Laureth-21 | 0.20 | 0.20 | 0.20 | 0.20 | 0.20 | 0.19 | 0.18 |
|  |  | Sodium lauroyl glutamate | 0.00 | 0.00 | 0.00 | 0.00 | 0.00 | 0.00 | 0.00 |
| C |  | Water | 49.03 | 48.98 | 48.78 | 48.54 | 47.11 | 45.33 | 42.15 |
| D |  | Tromethamine | 5.10 | 5.10 | 5.08 | 5.05 | 4.90 | 4.72 | 4.39 |
| Others |  | Sorbitol | 21.43 | 21.41 | 21.32 | 21.21 | 20.59 | 19.81 | 18.42 |
|  |  | Trehalose | 7.14 | 7.14 | 7.11 | 7.07 | 6.86 | 6.60 | 6.14 |
|  |  | Glycerol | 7.14 | 7.14 | 7.11 | 7.07 | 6.86 | 6.60 | 6.14 |
|  |  | PG | 5.10 | 5.10 | 5.08 | 5.05 | 4.90 | 4.72 | 4.39 |
|  |  | Mannitol | 4.08 | 4.08 | 4.06 | 4.04 | 3.92 | 3.77 | 3.51 |
|  |  | Acrylates/C10-30 alkyl acrylate crosspolymer | 0.17 | 0.17 | 0.17 | 0.17 | 0.17 | 0.16 | 0.15 |
|  |  | Phenoxyethanol | 0.20 | 0.20 | 0.20 | 0.20 | 0.20 | 0.19 | 0.18 |
|  |  | EDTA-2Na | 0.10 | 0.10 | 0.10 | 0.10 | 0.10 | 0.09 | 0.09 |
|  |  | Fragrance | 0.08 | 0.08 | 0.08 | 0.08 | 0.08 | 0.08 | 0.07 |
| Total |  |  | 100 | 100 | 100 | 100 | 100 | 100 | 100 |
| (A1) mass % in skin cleansing agent |  |  | 0.0008 | 0.01 | 0.04 | 0.08 | 0.29 | 0.57 | 1.05 |
| (A2) mass % in skin cleansing agent |  |  | 0.0023 | 0.02 | 0.11 | 0.23 | 0.88 | 1.70 | 3.16 |
| A1/A2 |  |  | 0.33 | 0.33 | 0.33 | 0.33 | 0.33 | 0.33 | 0.33 |

TABLE 3-continued

|  |  | Example 9 | Example 10 | Example 11 | Example 12 | Example 13 | Example 14 | Example 15 |
|---|---|---|---|---|---|---|---|---|
| Salt concentration (salt concentration with respect to water (C)) | | 10.6 | 10.6 | 10.6 | 10.6 | 10.6 | 10.6 | 10.6 |
| Evaluation | Sebum cleansing ability | 4 | 4 | 4 | 4 | 4 | 4 | 4 |
| | Rinsability | 4 | 4 | 4 | 4 | 4 | 3.75 | 3.75 |
| | Non-friction feeling | 4 | 4 | 4 | 4 | 4 | 3.5 | 3 |
| | Persistence of moist feeling | 3 | 3.25 | 3.5 | 3.75 | 4 | 4 | 4 |
| | Persistence of non-stretched feeling | 3 | 3.5 | 3.75 | 4 | 4 | 4 | 4 |
| | Persistence of softness | 3 | 3 | 3.5 | 3.75 | 4 | 4 | 3.75 |
| | Storage stability | 2 | 2 | 2 | 2 | 2 | 2 | 2 |

*GOHSENX T-330H, manufactured by Mitsubishi Chemical Corporation

TABLE 4

| | | | Example 16 | Example 17 | Example 18 | Example 19 | Example 20 | Example 21 | Comparative Example 1 | Comparative Example 2 | Comparative Example 3 | Comparative Example 4 | Comparative Example 5 |
|---|---|---|---|---|---|---|---|---|---|---|---|---|---|
| A | A1 | Dipentaerythrityl tripolyhydroxystearate | 7.5 | 7.5 | 7.5 | 7.5 | 7.5 | 7.5 | | | | | 7.5 |
| | | Cholesteryl hydroxystearate | | | | | | | | | | | |
| | A2 | Squalane | 15.0 | 15.0 | 15.0 | 15.0 | 15.0 | 15.0 | | 30.0 | | | 15.0 |
| | | Petrolatum | 7.5 | 7.5 | 7.5 | 7.5 | 7.5 | 7.5 | | | | | 7.5 |
| | | Glycerol | | | | | | | 30.0 | | | | |
| | A3 | Sodium (maleic acid/vinyl alcohol) copolymer* | 59.4 | 59.4 | 59.4 | 59.4 | 59.4 | 59.4 | 59.4 | 59.4 | 84.9 | | 59.4 |
| | Others | Polyoxyethylene (20EO) sorbitan monostearate | 6.8 | 6.8 | 6.8 | 6.8 | 6.8 | 6.8 | 6.8 | 6.8 | 9.7 | | 6.8 |
| | | Sorbitan stearate | 2.3 | 2.3 | 2.3 | 2.3 | 2.3 | 2.3 | 2.3 | 2.3 | 3.3 | | 2.3 |
| | | Water | 1.5 | 1.5 | 1.5 | 1.5 | 1.5 | 1.5 | 1.5 | 1.5 | 2.1 | | 1.5 |
| Total | | | 100.0 | 100.0 | 100.0 | 100.0 | 100.0 | 100.0 | 100.0 | 100.0 | 100.0 | 0 | 100.0 |
| Amount to be added to skin cleansing agent | | | 2 | 2 | 2 | 2 | 2 | 2 | 2 | 2 | 2 | | 2 |
| A | A1 | Dipentaerythrityl tripolyhydroxystearate | 0.15 | 0.14 | 0.15 | 0.15 | 0.14 | 0.14 | 0.00 | 0.60 | 0.00 | 0.15 | 0.16 |
| | | Cholesteryl hydroxystearate | 0.00 | 0.00 | 0.00 | 0.00 | 0.00 | 0.00 | 0.00 | 0.00 | 0.00 | 0.00 | 0.00 |
| | A2 | Squalane | 0.30 | 0.29 | 0.30 | 0.31 | 0.29 | 0.29 | 0.00 | 0.00 | 0.00 | 0.30 | 0.32 |
| | | Petrolatum | 0.15 | 0.14 | 0.15 | 0.15 | 0.14 | 0.14 | 0.00 | 0.00 | 0.00 | 0.15 | 0.16 |
| | | Glycerol | 0.00 | 0.00 | 0.00 | 0.00 | 0.00 | 0.00 | 0.60 | 0.00 | 0.00 | 0.00 | 0.00 |
| | A3 | Sodium (maleic acid/vinyl alcohol) copolymer* | 1.19 | 1.14 | 1.19 | 1.22 | 1.13 | 1.13 | 1.19 | 1.19 | 1.70 | 0.00 | 1.26 |
| | Others | Polyoxyethylene (20EO) sorbitan monostearate | 0.14 | 0.13 | 0.14 | 0.14 | 0.13 | 0.13 | 0.14 | 0.14 | 0.19 | 0.00 | 0.14 |
| | | Sorbitan stearate | 0.05 | 0.04 | 0.05 | 0.05 | 0.04 | 0.04 | 0.05 | 0.05 | 0.07 | 0.00 | 0.05 |
| | | Water | 0.03 | 0.03 | 0.03 | 0.03 | 0.03 | 0.03 | 0.03 | 0.03 | 0.04 | 0.00 | 0.03 |
| B | | Steareth-13 | 0.00 | 0.00 | 0.20 | 0.21 | 0.19 | 0.19 | 0.20 | 0.20 | 0.20 | 0.20 | 0.00 |
| | | Laureth-21 | 0.00 | 0.00 | 0.20 | 0.21 | 0.19 | 0.19 | 0.20 | 0.20 | 0.20 | 0.20 | 0.00 |
| | | Sodium lauroyl glutamate | 0.40 | 4.78 | 5.00 | 0.00 | 4.76 | 0.00 | 0.00 | 0.00 | 0.00 | 0.00 | 0.00 |
| C | | Water | 48.05 | 45.94 | 48.05 | 49.28 | 45.76 | 45.76 | 48.05 | 48.05 | 48.05 | 48.73 | 50.79 |
| D | | Tromethamine | 5.00 | 4.78 | 0.00 | 2.56 | 4.76 | 9.52 | 5.00 | 5.00 | 5.00 | 5.07 | 0.00 |
| Others | | Sorbitol | 21.00 | 20.08 | 21.00 | 21.54 | 20.00 | 20.00 | 21.00 | 21.00 | 21.00 | 21.30 | 22.20 |
| | | Trehalose | 7.00 | 6.69 | 7.00 | 7.18 | 6.67 | 6.67 | 7.00 | 7.00 | 7.00 | 7.10 | 7.40 |
| | | Glycerol | 7.00 | 6.69 | 7.00 | 7.18 | 6.67 | 6.67 | 7.00 | 7.00 | 7.00 | 7.10 | 7.40 |
| | | PG | 5.00 | 4.78 | 5.00 | 5.13 | 4.76 | 4.76 | 5.00 | 5.00 | 5.00 | 5.07 | 5.29 |
| | | Mannitol | 4.00 | 3.82 | 4.00 | 4.10 | 3.81 | 3.81 | 4.00 | 4.00 | 4.00 | 4.06 | 4.23 |
| | | Acrylates/C10-30 alkyl acrylate crosspolymer | 0.17 | 0.16 | 0.17 | 0.17 | 0.16 | 0.16 | 0.17 | 0.17 | 0.17 | 0.17 | 0.18 |
| | | Phenoxyethanol | 0.20 | 0.19 | 0.20 | 0.21 | 0.19 | 0.19 | 0.20 | 0.20 | 0.20 | 0.20 | 0.21 |
| | | EDTA-2Na | 0.10 | 0.10 | 0.10 | 0.10 | 0.10 | 0.10 | 0.10 | 0.10 | 0.10 | 0.10 | 0.11 |
| | | Fragrance | 0.08 | 0.08 | 0.08 | 0.08 | 0.08 | 0.08 | 0.08 | 0.08 | 0.08 | 0.08 | 0.08 |
| Total | | | 100 | 100 | 100 | 100 | 100 | 100 | 100 | 100 | 100 | 100 | 100 |
| (A1) mass % in skin cleansing agent | | | 0.15 | 0.14 | 0.15 | 0.15 | 0.14 | 0.14 | 0.00 | 0.60 | 0.00 | 0.15 | 0.16 |
| (A2) mass % in skin cleansing agent | | | 0.45 | 0.43 | 0.45 | 0.46 | 0.43 | 0.43 | 0.00 | 0.00 | 0.00 | 0.46 | 0.48 |
| A1/A2 | | | 0.33 | 0.33 | 0.33 | 0.33 | 0.33 | 0.33 | — | — | — | 0.33 | 0.33 |

TABLE 4-continued

| | Example 16 | Example 17 | Example 18 | Example 19 | Example 20 | Example 21 | Comparative Example 1 | Comparative Example 2 | Comparative Example 3 | Comparative Example 4 | Comparative Example 5 |
|---|---|---|---|---|---|---|---|---|---|---|---|
| Salt concentration (salt concentration with respect to water (C)) | 11.4 | 21.0 | 10.6 | 5.4 | 21.0 | 21.0 | 10.6 | 10.6 | 10.6 | 10.6 | 0.2 |
| Evaluation Sebum cleansing ability | 4 | 4 | 4 | 3 | 4 | 4 | 4 | 4 | 4 | 4 | 2 |
| Rinsability | 4 | 3.5 | 4 | 4 | 4 | 4 | 3.5 | 4 | 4 | 2 | 3.5 |
| Non-friction feeling | 4 | 3.75 | 3.75 | 4 | 3.75 | 4 | 2 | 2 | 2 | 2 | 4 |
| Persistence of moist feeling | 4 | 3.5 | 3.75 | 4 | 3.75 | 4 | 2 | 2 | 2 | 1 | 4 |
| Persistence of non-stretched feeling | 4 | 3.75 | 3.75 | 4 | 3.75 | 4 | 2 | 2 | 2 | 2 | 4 |
| Persistence of softness | 4 | 3.75 | 3.75 | 2 | 3.75 | 4 | 2 | 2 | 2 | 1 | 4 |
| Storage stability | 2 | 2 | 2 | 2 | 2 | 2 | 2 | 2 | 2 | 1 | 2 |

*GOHSENX T-330H, manufactured by Mitsubishi Chemical Corporation

TABLE 5

| | | | Example 1 | Example 2 | Example 22 | Example 23 | Example 3 | Example 5 | Example 6 | Example 24 | Example 25 | Example 26 | Example 27 |
|---|---|---|---|---|---|---|---|---|---|---|---|---|---|
| A | A1 | Erythrityl tripolyhydroxystearate | 7.5 | | | | 7.5 | 7.5 | 7.5 | 7.5 | 7.5 | 7.5 | 7.5 |
| | | Cholesteryl hydroxystearate | | 7.5 | | | | | | | | | |
| | | Phytosteryl/decyltetradecyl myristoylmethyl-β-alanine | | | 7.5 | | | | | | | | |
| | | Di(cholesteryl/behenyl/octyldodecyl) lauroyl glutamate | | | | 7.5 | | | | | | | |
| | A2 | Squalane | 15.0 | 15.0 | 15.0 | 15.0 | | 22.5 | | | | | |
| | | Petrolatum | 7.5 | 7.5 | 7.5 | 7.5 | 22.5 | | | | | | |
| | | Glycerol | | | | | | | 22.5 | | | | |
| | | Liquid paraffin | | | | | | | | 22.5 | | | |
| | | Isostearyl isostearate | | | | | | | | | 22.5 | | |
| | | Neopentyl glycol dicaprate | | | | | | | | | | 22.5 | |
| | | Jojoba oil | | | | | | | | | | | 22.5 |
| | A3 | Sodium (maleic acid/vinyl alcohol) copolymer* | 59.4 | 59.4 | 59.4 | 59.4 | 59.4 | 59.4 | 59.4 | 59.4 | 59.4 | 59.4 | 59.4 |
| | Others | Polysorbate 60 | 6.8 | 6.8 | 6.8 | 6.8 | 6.8 | 6.8 | 6.8 | 6.8 | 6.8 | 6.8 | 6.8 |
| | | Sorbitan stearate | 2.3 | 2.3 | 2.3 | 2.3 | 2.3 | 2.3 | 2.3 | 2.3 | 2.3 | 2.3 | 2.3 |
| | | Water | 1.5 | 1.5 | 1.5 | 1.5 | 1.5 | 1.5 | 1.5 | 1.5 | 1.5 | 1.5 | 1.5 |
| Total | | | 100.0 | 100.0 | 100.0 | 100.0 | 100.0 | 100.0 | 100.0 | 100.0 | 100.0 | 100.0 | 100.0 |
| Amount to be added to skin cleansing agent | | | 2 | 2 | 2 | 2 | 2 | 2 | 2 | 2 | 2 | 2 | 2 |
| A | A1 | Erythrityl tripolyhydroxystearate | 0.15 | 0 | 0 | 0 | 0.15 | 0.15 | 0.15 | 0.15 | 0.15 | 0.15 | 0.15 |
| | | Cholesteryl hydroxystearate | 0 | 0.15 | 0 | 0 | 0 | 0 | 0 | 0 | 0 | 0 | 0 |
| | | Phytosteryl/decyltetradecyl myristoylmethyl-β-alanine | | | 0.15 | 0 | | | | | | | |
| | | Di(cholesteryl/behenyl/octyldodecyl) lauroyl glutamate | | | 0 | 0.15 | | | | | | | |
| | A2 | Squalane | 0.30 | 0.30 | 0.30 | 0.30 | 0 | 0.45 | 0 | 0 | 0 | 0 | 0 |
| | | Petrolatum | 0.15 | 0.15 | 0.15 | 0.15 | 0.45 | 0 | 0 | 0 | 0 | 0 | 0 |
| | | Glycerol | 0 | 0 | 0 | 0 | 0 | 0 | 0.45 | 0 | 0 | 0 | 0 |
| | | Liquid paraffin | | | | | | | | 0.45 | 0 | 0 | 0 |
| | | Isostearyl isostearate | | | | | | | | 0 | 0.45 | 0 | 0 |
| | | Neopentyl glycol dicaprate | | | | | | | | 0 | 0 | 0.45 | 0 |
| | | Jojoba oil | | | | | | | | 0 | 0 | 0 | 0.45 |
| | A3 | Sodium (maleic acid/vinyl alcohol) copolymer* | 1.188 | 1.188 | 1.188 | 1.188 | 1.188 | 1.188 | 1.188 | 1.188 | 1.188 | 1.188 | 1.188 |
| | Others | Polysorbate 60 | 0.136 | 0.136 | 0.136 | 0.136 | 0.136 | 0.136 | 0.136 | 0.136 | 0.136 | 0.136 | 0.136 |
| | | Sorbitan stearate | 0.046 | 0.046 | 0.046 | 0.046 | 0.046 | 0.046 | 0.046 | 0.046 | 0.046 | 0.046 | 0.046 |
| | | Water | 0.03 | 0.03 | 0.03 | 0.03 | 0.03 | 0.03 | 0.03 | 0.03 | 0.03 | 0.03 | 0.03 |
| B | | Steareth-13 | 0.2 | 0.2 | 0.2 | 0.2 | 0.2 | 0.2 | 0.2 | 0.2 | 0.2 | 0.2 | 0.2 |
| | | Laureth-21 | 0.2 | 0.2 | 0.2 | 0.2 | 0.2 | 0.2 | 0.2 | 0.2 | 0.2 | 0.2 | 0.2 |
| | | Sodium lauroyl glutamate | | | | | | | | | | | |
| C | | Water | 48.05 | 48.05 | 48.05 | 48.05 | 48.05 | 48.05 | 48.05 | 48.05 | 48.05 | 48.05 | 48.05 |
| D | | Tromethamine | 5 | 5 | 5 | 5 | 5 | 5 | 5 | 5 | 5 | 5 | 5 |
| Others | | Sorbitol | 21 | 21 | 21 | 21 | 21 | 21 | 21 | 21 | 21 | 21 | 21 |
| | | Trehalose | 7 | 7 | 7 | 7 | 7 | 7 | 7 | 7 | 7 | 7 | 7 |
| | | Glycerol | 7 | 7 | 7 | 7 | 7 | 7 | 7 | 7 | 7 | 7 | 7 |
| | | PG | 5 | 5 | 5 | 5 | 5 | 5 | 5 | 5 | 5 | 5 | 5 |
| | | Mannitol | 4 | 4 | 4 | 4 | 4 | 4 | 4 | 4 | 4 | 4 | 4 |
| | | Acrylates/C10-30 alkyl acrylate crosspolymer | 0.17 | 0.17 | 0.17 | 0.17 | 0.17 | 0.17 | 0.17 | 0.17 | 0.17 | 0.17 | 0.17 |
| | | Phenoxyethanol | 0.2 | 0.2 | 0.2 | 0.2 | 0.2 | 0.2 | 0.2 | 0.2 | 0.2 | 0.2 | 0.2 |
| | | EDTA-2Na | 0.1 | 0.1 | 0.1 | 0.1 | 0.1 | 0.1 | 0.1 | 0.1 | 0.1 | 0.1 | 0.1 |
| | | Fragrance | 0.08 | 0.08 | 0.08 | 0.08 | 0.08 | 0.08 | 0.08 | 0.08 | 0.08 | 0.08 | 0.08 |
| Total | | | 100 | 100 | 100 | 100 | 100 | 100 | 100 | 100 | 100 | 100 | 100 |
| (A1) mass % in skin cleansing agent | | | 0.15 | 0.15 | 0.15 | 0.15 | 0.15 | 0.15 | 0.15 | 0.15 | 0.15 | 0.15 | 0.15 |
| (A2) mass % in skin cleansing agent | | | 0.45 | 0.45 | 0.45 | 0.45 | 0.45 | 0.45 | 0.45 | 0.45 | 0.45 | 0.45 | 0.45 |
| A1/A2 | | | 0.33 | 0.33 | 0.33 | 0.33 | 0.33 | 0.33 | 0.33 | 0.33 | 0.33 | 0.33 | 0.33 |
| Salt concentration (salt concentration with respect to water (C)) | | | 10.6 | 10.6 | 10.6 | 10.6 | 10.6 | 10.6 | 10.6 | 10.6 | 10.6 | 10.6 | 10.6 |
| Evaluation | | Sebum cleansing ability | 4 | 4 | 3 | 4 | 4 | 4 | 4 | 3 | 3 | 4 | 4 |
| | | Rinsability | 4 | 4 | 4 | 4 | 4 | 4 | 4 | 4 | 4 | 4 | 4 |
| | | Non-friction feeling | 4 | 4 | 4 | 4 | 4 | 4 | 3.5 | 3.5 | 4.0 | 3.75 | 3.75 |
| | | Persistence of moist feeling | 4 | 4 | 4 | 4 | 4 | 3.5 | 3 | 4 | 4 | 4 | 4 |
| | | Persistence of non-stretched feeling | 4 | 4 | 4 | 4 | 3.5 | 4 | 3 | 4 | 3 | 4 | 4 |
| | | Persistence of softness | 4 | 3.75 | 3.75 | 4 | 3.75 | 4 | 3.5 | 3.5 | 3.75 | 3.75 | 4 |
| | | Storage stability | 2 | 2 | 2 | 2 | 2 | 2 | 2 | 2 | 2 | 2 | 2 |

*GOHSENX T-330H, manufactured by Mitsubishi Chemical Corporation

TABLE 6

| | | | Example 1 | Example 7 | Example 8 | Example 28 | Example 29 | Example 30 | Example 31 | Example 32 | Example 33 | Example 34 | Example 35 | Example 36 |
|---|---|---|---|---|---|---|---|---|---|---|---|---|---|---|
| A | A1 | Erythrityl tripolyhydroxystearate | 7.5 | 27.0 | 3.0 | 13.6 | 29.4 | 28.6 | 15.0 | 29.0 | 5.0 | 1.4 | 0.1 | 0.3 |
| | | Cholesteryl hydroxystearate | | | | | | | | | | | | |
| | A2 | Squalane | 15.0 | 0 | 0 | 0 | 0 | 0 | 0 | 0 | 0 | 0 | 0 | 0.0 |
| | | Petrolatum | 7.5 | 3 | 27 | 16.4 | 0.6 | 1.4 | 15.0 | 1.0 | 25.0 | 28.6 | 29.9 | 29.7 |
| | | Glycerol | | | | | | | | | | | | |
| | A3 | Sodium (maleic acid/vinyl alcohol) copolymer* | 59.4 | 59.4 | 59.4 | 59.4 | 59.4 | 59.4 | 59.4 | 59.4 | 59.4 | 59.4 | 59.4 | 59.4 |
| | Others | Polysorbate 60 | 6.8 | 6.8 | 6.8 | 6.8 | 6.8 | 6.8 | 6.8 | 6.8 | 6.8 | 6.8 | 6.8 | 6.8 |
| | | Sorbitan stearate | 2.3 | 2.3 | 2.3 | 2.3 | 2.3 | 2.3 | 2.3 | 2.3 | 2.3 | 2.3 | 2.3 | 2.3 |
| | | Water | 1.5 | 1.5 | 1.5 | 1.5 | 1.5 | 1.5 | 1.5 | 1.5 | 1.5 | 1.5 | 1.5 | 1.5 |
| Total | | | 100.0 | 100.0 | 100.0 | 100.0 | 100.0 | 100.0 | 100.0 | 100.0 | 100.0 | 100.0 | 100.0 | 100.0 |
| Amount to be added to skin cleansing agent | | | | | | | | | | | | | | |
| A | A1 | Erythrityl tripolyhydroxystearate | 2 | 2 | 2 | 73.33 | 34 | 24.5 | 33.34 | 10.33 | 40 | 52.5 | 67 | 10.1 |
| | | Cholesteryl hydroxystearate | 0.15 | 0.54 | 0.06 | 10.00 | 10.00 | 7.00 | 5.00 | 3.00 | 2.00 | 0.75 | 0.10 | 0.03 |
| | A2 | Squalane | 0.00 | 0.00 | 0.00 | 0.00 | 0.00 | 0.00 | 0.00 | 0.00 | 0.00 | 0.00 | 0.00 | 0.00 |
| | | Petrolatum | 0.30 | 0.00 | 0.00 | 0.00 | 0.00 | 0.00 | 0.00 | 0.10 | 0.00 | 0.00 | 0.00 | 0.00 |
| | | Glycerol | 0.15 | 0.06 | 0.54 | 12.00 | 0.20 | 0.35 | 5.00 | 0.00 | 10.00 | 15.00 | 20.00 | 3.00 |
| | A3 | Sodium (maleic acid/vinyl alcohol) copolymer* | 1.19 | 1.19 | 1.19 | 43.56 | 20.20 | 14.55 | 19.80 | 6.14 | 23.76 | 31.19 | 39.80 | 6.00 |
| | Others | Polysorbate 60 | 0.14 | 0.14 | 0.14 | 4.99 | 2.31 | 1.67 | 2.27 | 0.70 | 2.72 | 3.57 | 4.56 | 0.69 |
| | | Sorbitan stearate | 0.05 | 0.05 | 0.05 | 1.69 | 0.78 | 0.56 | 0.77 | 0.24 | 0.92 | 1.21 | 1.54 | 0.23 |
| | | Water | 0.03 | 0.03 | 0.03 | 1.10 | 0.51 | 0.37 | 0.50 | 0.15 | 0.60 | 0.79 | 1.01 | 0.15 |
| B | | Steareth-13 | 0.20 | 0.20 | 0.20 | 0.20 | 0.20 | 0.20 | 0.20 | 0.20 | 0.20 | 0.20 | 0.20 | 0.20 |
| | | Laureth-21 | 0.20 | 0.20 | 0.20 | 0.20 | 0.20 | 0.20 | 0.20 | 0.20 | 0.20 | 0.20 | 0.20 | 0.20 |
| | | Sodium lauroyl glutamate | 0.00 | 0.00 | 0.00 | 0.00 | 0.00 | 0.00 | 0.00 | 0.00 | 0.00 | 0.00 | 0.00 | 0.00 |
| C | | Water | 48.05 | 48.05 | 48.05 | 15.72 | 16.05 | 25.55 | 16.71 | 39.72 | 17.05 | 18.55 | 15.05 | 39.95 |
| D | | Tromethamine | 5.00 | 5.00 | 5.00 | 5.00 | 5.00 | 5.00 | 5.00 | 5.00 | 5.00 | 5.00 | 5.00 | 5.00 |
| Others | | Sorbitol | 21.00 | 21.00 | 21.00 | 0.00 | 21.00 | 21.00 | 21.00 | 21.00 | 21.00 | 0.00 | 0.00 | 21.00 |
| | | Trehalose | 7.00 | 7.00 | 7.00 | 0.00 | 7.00 | 7.00 | 7.00 | 7.00 | 7.00 | 7.00 | 7.00 | 7.00 |
| | | Glycerol | 7.00 | 7.00 | 7.00 | 0.00 | 7.00 | 7.00 | 7.00 | 7.00 | 7.00 | 7.00 | 0.00 | 7.00 |
| | | PG | 5.00 | 5.00 | 5.00 | 5.00 | 5.00 | 5.00 | 5.00 | 5.00 | 5.00 | 5.00 | 5.00 | 5.00 |
| | | Mannitol | 4.00 | 4.00 | 4.00 | 0.00 | 4.00 | 4.00 | 4.00 | 4.00 | 4.00 | 4.00 | 0.00 | 4.00 |
| | | Acrylates/C10-30 alkyl acrylate crosspolymer | 0.17 | 0.17 | 0.17 | 0.17 | 0.17 | 0.17 | 0.17 | 0.17 | 0.17 | 0.17 | 0.17 | 0.17 |
| | | Phenoxyethanol | 0.20 | 0.20 | 0.20 | 0.20 | 0.20 | 0.20 | 0.20 | 0.20 | 0.20 | 0.20 | 0.20 | 0.20 |
| | | EDTA-2Na | 0.10 | 0.10 | 0.10 | 0.10 | 0.10 | 0.10 | 0.10 | 0.10 | 0.10 | 0.10 | 0.10 | 0.10 |
| | | Fragrance | 0.08 | 0.08 | 0.08 | 0.08 | 0.08 | 0.08 | 0.08 | 0.08 | 0.08 | 0.08 | 0.08 | 0.08 |
| Total | | | 100 | 100 | 100 | 100 | 100 | 100 | 100 | 100 | 100 | 100 | 100 | 100 |
| (A1) mass % in skin cleansing agent | | | 0.15 | 0.54 | 0.06 | 10.00 | 10.00 | 7.00 | 5.00 | 3.00 | 2.00 | 0.75 | 0.10 | 0.03 |
| (A2) mass % in skin cleansing agent | | | 0.45 | 0.06 | 0.54 | 12.00 | 0.2 | 0.35 | 5.00 | 0.10 | 10.00 | 15.00 | 20.00 | 3.00 |
| A1/A2 | | | 0.33 | 9.00 | 0.11 | 0.83 | 50.00 | 20.00 | 1.00 | 30.00 | 0.20 | 0.05 | 0.005 | 0.01 |

TABLE 6-continued

| | Example 1 | Example 7 | Example 8 | Example 28 | Example 29 | Example 30 | Example 31 | Example 32 | Example 33 | Example 34 | Example 35 | Example 36 |
|---|---|---|---|---|---|---|---|---|---|---|---|---|
| Salt concentration (salt concentration with respect to water (C)) | 10.6 | 10.6 | 10.6 | 32.4 | 31.8 | 20.0 | 30.5 | 12.8 | 29.9 | 27.5 | 33.9 | 12.8 |
| Evaluation Sebum cleansing ability | 4 | 4 | 4 | 4 | 4 | 4 | 4 | 4 | 4 | 4 | 4 | 4 |
| Rinsability | 4 | 4 | 3.75 | 3 | 3.25 | 3 | 3.25 | 3 | 3 | 3 | 3 | 3 |
| Non-friction feeling | 4 | 3.5 | 3.75 | 4 | 3 | 3 | 3 | 3.0 | 3 | 3 | 3 | 3 |
| Persistence of moist feeling | 4 | 3.75 | 3.5 | 4 | 4 | 4 | 4 | 4 | 4 | 4 | 3.75 | 4 |
| Persistence of non-stretched feeling | 4 | 3.75 | 3.5 | 4 | 4 | 4 | 4 | 4 | 4 | 4 | 4 | 4 |
| Persistence of softness | 4 | 3.5 | 3.75 | 4 | 3.75 | 3.75 | 4 | 3.5 | 4 | 4 | 4 | 4 |
| Storage stability | 2 | 2 | 2 | 2 | 2 | 2 | 2 | 2 | 2 | 2 | 2 | 2 |

*GOHSENX T-330H, manufactured by Mitsubishi Chemical Corporation

The invention claimed is:

1. A skin cleansing agent, comprising:
   a particle (A), comprising:
   a water-holding oil agent (A1) in an amount of from 0.0001 to 13 mass % in the skin cleansing agent;
   a moisturizing agent (A1) an amount of from 0.001 to 25 mass % in the skin cleansing agent; and
   a polymer (A3);
   a surfactant (B); and
   water (C),
   wherein
   the water-holding oil agent (A1) comprises at least one selected from the group consisting of a dimer acid ester, a pentaerythritol fatty acid ester, a fatty acid cholesterol ester having from 16 to 22 carbon atoms, a phytosterol ester having from 16 to 22 carbon atoms, and an N-acyl amino acid ester,
   the polymer (A3) is a salt-sensitive polymer,
   a mass ratio of the water-holding oil agent (A1) to the moisturizing agent (A2), (A1)/(A2), is from 0.004 to 60, and
   the particle (A) has an average particle diameter of from 1 to 1500 μm.

2. The skin cleansing agent according to claim 1, wherein the water-holding oil agent (A1) can hold water equal to or more than its own weight at 50° C.

3. The skin cleansing agent according to claim 1, wherein the water-holding oil agent (A1) comprises at least one selected from the group consisting of dipentaerythrityl tripolyhydroxystearate, cholesteryl hydroxystearate, phytosteryl/decyltetradecyl N-myristoyl-N-methylalanine, and di(cholesteryl/behenyl/octyldodecyl) N-lauroyl-L-glutamate.

4. The skin cleansing agent according to claim 1, wherein the moisturizing agent (A2) comprises at least one oily moisturizing agent.

5. The skin cleansing agent according to claim 1, wherein the moisturizing agent (A2) comprises at least one selected from the group consisting of a hydrocarbon oil an ester oil other than the (A1), and a higher alcohol having at least 10 carbon atoms.

6. The skin cleansing agent according to claim 1, wherein the moisturizing agent (A2) comprises at least one selected from the group consisting of squalane, petrolatum, liquid paraffin, isostearyl isostearate, neopentyl glycol dicaprate, jojoba oil, and glycerol.

7. The skin cleansing agent according to claim 1, wherein the polymer (A3) is an acid-modified polyvinyl alcohol.

8. The skin cleansing agent according to claim 1, wherein the polymer (A3) comprises an acid-modified polyvinyl alcohol having introduced therein at least one selected from the group consisting of a sulfonic acid group and a carboxylic acid group.

9. The skin cleansing agent according to claim 1, further comprising (D) at least one selected from the group consisting of 2-amino-2-hydroxymethyl-1,3-propanediol, 2-amino-2-methyl-1-propanol, 2-amino-2-methyl-1,3-propanediol, and arginine.

10. The skin cleansing agent according to claim 1, wherein a content of the water-holding oil agent (A1) in the skin cleansing agent is from 0.001 to 5 mass %, and a content of the moisturizing agent (A2) in the skin cleansing agent is from 0.01 to 10 mass %.

11. The skin cleansing agent according to claim 1, wherein a salt content in the skin cleansing agent based on a content of water is from 2 to 70 mass %.

12. A method for cleansing the skin, the method comprising applying the skin cleansing agent according to claim 1 to the skin, and then rinsing with water.

* * * * *